United States Patent [19]

Reilly et al.

[11] Patent Number: 5,409,926
[45] Date of Patent: Apr. 25, 1995

[54] AT-2 ANTAGONIST INHIBITION OF VASCULAR RESTENOSIS

[75] Inventors: Christopher F. Reilly, Wilmslow, England; Stephen E. Delaszlo, Rumson, N.J.; Robert G. Johnson, Rosemont; Tsuneo Fujita, King of Prussia, both of Pa.

[73] Assignee: Merck & Co., Inc., Rahway, N.J.

[21] Appl. No.: 93,833

[22] Filed: Jul. 19, 1993

[51] Int. Cl.$^6$ .................................. A61K 31/505
[52] U.S. Cl. .................. 514/234.8; 514/232.5; 514/232.8; 514/255; 514/259
[58] Field of Search ............... 514/232.5, 234.8, 255, 514/259, 232.8

[56]  References Cited

U.S. PATENT DOCUMENTS

| | | | |
|---|---|---|---|
| 5,162,325 | 11/1992 | Chakravarty et al. | 514/259 |
| 5,238,942 | 8/1993 | Chakravarty et al. | |
| 5,240,928 | 8/1993 | Allen et al. | 514/259 |
| 5,246,943 | 9/1993 | Blankley et al. | 514/307 |
| 5,276,048 | 1/1994 | Hodges et al. | 514/381 |

FOREIGN PATENT DOCUMENTS

| | | |
|---|---|---|
| 0411766A1 | of 0000 | European Pat. Off. |
| 0465368A1 | of 0000 | European Pat. Off. |
| 0512870A1 | of 0000 | European Pat. Off. |
| 0518426A1 | of 0000 | European Pat. Off. |
| WO93/00341 | of 0000 | WIPO |
| WO93/08171 | of 0000 | WIPO |

OTHER PUBLICATIONS

Hypertension, vol. 20, p. 737 (1992).

J. Pharmacology and Exp. Therapeutics, vol. 225, No. 3 (1983) pp. 584–592, J. R. Shepard et al.

*Primary Examiner*—Marianne M. Cintins
*Assistant Examiner*—William R. A. Jarvis

[57] ABSTRACT

Novel disubstituted 6-aminoquinazolinones of the Formula

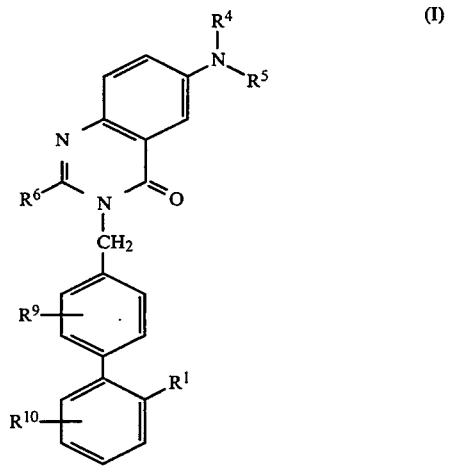

are useful as angiotensin-II receptor (subtype 2) antagonists ($AT_2$ antagonists) alone or in combination with heparin, and can act to suppress the vascular stenosis which commonly occurs during the development of atherosclerosis and the restenosis following arterial angioplasty, stent placement, bypass surgery, heart transplantation or endarterectomy.

10 Claims, No Drawings

AT-2 ANTAGONIST INHIBITION OF VASCULAR RESTENOSIS

BACKGROUND OF THE INVENTION

Restenosis occurs after a variety of arterial insults such as angioplasty, stent placement, bypass surgery, heart transplantation and endarterectomy. Some of these procedures have been practiced for years for the treatment of coronary artery disease. Despite good initial successes and few complications, physiologically significant restenosis occurs between one and six months after treatment at the site of the procedures in a number of patients, and continues to be the main problem associated with the procedures.

To date, pharmacological intervention directed toward inhibiting restenosis has been largely unsuccessful including the use of corticosteroids, antiplatelet agents, calcium channel blockers, anticoagulant therapy, hypocholesterolemic agents and fish oil preparation.

There are data to indicate that there are similarities between native arterial lesions and those induced by surgical procedures and that treatment with angiotensin II site 2 receptor ($AT_2$) antagonists alone or in combination with heparin or a derivative thereof will prevent or at least slow down the rate of restenosis.

Further, some specific $AT_2$ antagonists of other structures than described herein, are described as being useful in restenosis in *Hypertension*, 20, p. 737 (1992).

DETAILED DESCRIPTION OF THE INVENTION

The novel method of treatment of this invention comprises the administration to a patient scheduled to undergo an arterial surgical procedure such as arterial angioplasty, stent placement, bypass surgery, heart transplantation or endarterectomy, an $AT_2$ antagonist of specific structure described herein, about 0-48 hours before the surgical procedure and for an indefinite period of time after the procedure, whereby restenosis is inhibited.

In the novel method of this invention the patient is human scheduled for the arterial surgery.

The dose of $AT_2$ antagonist is about 50 to about 200 mg/day preferably about 100 mg/day, both before and after the surgical procedure. Treatment with the $AT_2$ antagonist after the angioplasty continues for at least 6 months and may be required indefinitely to prevent restenosis.

In the novel method of treatment of this invention, the $AT_2$ antagonist may be utilized in compositions such as tablets, capsules or elixirs for oral administration, suppositories for rectal administration, steril solutions or suspensions for parenteral or intramuscular administration or the like.

The structure of the $AT_2$ antagonist is provided herein and has an intrinsic activity of about IC50<10 nM. These known $AT_2$ antagonists of the quinazolinone type, described below, are disclosed as antihypertensives in European patent publication EP 518,426 published Dec. 16, 1992, and U.S. Ser. No. 07/912,458, filed Jul. 13, 1992 now abandoned. However, there is no disclosure of the property of restenosis inhibition in the prior art for these specific compounds.

The compounds, of the instantly claimed method have the general formula (I);

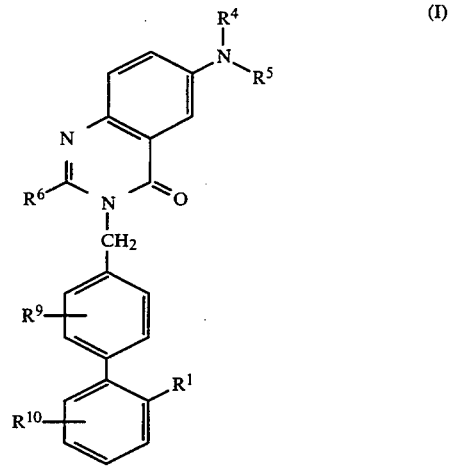

or a pharmaceutically acceptable salt thereof, wherein:

$R^1$ is
(a) $CO_2R^2$
(b) tetrazol-5-yl;

$R^2$ is
(a) hydrogen, or
(b) $C_1$-$C_6$ alkyl;

$R^4$ is
(a) $C_1$-$C_6$ alkyl,
(b) substituted $C_1$-$C_6$ alkyl in which the substituent is halo, ($C_3$-$C_7$) cycloalkyl, $C_1$-$C_4$ alkoxy, hydroxy, di-($C_1$-$C_4$ alkyl)amino, morpholinyl, $C_1$-$C_4$ alkylpipemzinyl, $CF_3$, $C_1$-$C_4$ alkylthio, $C_1$-$C_4$ alkylsulfinyl, $C_1$-$C_4$ alkylsulfonyl, —CHO, $O(C_2$-$C_3$ alkyl-O—)n $C_1$-$C_3$ alkyl, where n=1-5,
(c) $C_2$-$C_6$ alkenyl,
(d) phenyl $C_1$-$C_6$ alkyl,
(e) heteroaryl $C_1$-$C_6$ alkyl;

$R^5$ is
(a) $CO_2R^7$,
(b) $COR^8$;

$R^6$ is
(a) H,
(b) methyl,
(c) ethyl,
(d) $C_4$-$C_6$ alkyl, excluding linear alkyl,
(e) $C_1$-$C_6$ cycloalkyl,
(f) $C_1$-$C_6$ branched alkyl, substituted with $C_1$-$C_4$ alkoxy;

$R^7$ is
(a) $C_1$-$C_6$ alkyl,
(b) substituted $C_1$-$C_6$ alkyl in which the substituent is $C_1$-$C_4$ alkoxy, hydroxy, halo (F, Cl, Br, I) di($C_1$-$C_4$ alkyl)amino, morpholinyl, $C_1$-$C_4$ alkylpiperazinyl, $C_1$-$C_4$ alkylsulfinyl, $C_1$-$C_4$ alkylsulfonyl, $C_1$-$C_4$ alkylthio, or $O(C_2$-$C_3$alkyl-O—)$_n$ $C_1$-$C_3$ alkyl, $C_3$-$C_7$ cycloalkyl, wherein n=1-5,
(c) phenyl $C_1$-$C_6$ alkyl,
(d) heteroaryl $C_1$-$C_6$ alkyl;

$R^8$ is
(a) phenyl
(b) phenyl $C_1$-$C_6$ alkyl,
(c) heteroaryl,
(d) heteroaryl $C_1$-$C_6$ alkyl,
(e) $C_1$-$C_6$ alkyl,
(f) substituted $C_1$-$C_6$ alkyl in which the substituent is halo (F, Cl, Br, I), $C_3$-$C_7$ cycloalkyl, $C_1$-$C_4$ alkoxy, hydroxy, di-($C_1$-$C_4$ alkyl)amino, morpholinyl, $C_1$-$C_4$ alkylpiperazinyl, $CF_3$, $C_1$-$C_4$ alkylthio, $C_1$-$C_4$ alkylsulfinyl, $C_1$-$C_4$ alkylsulfonyl, imidazolyl, —N($COC_1$-$C_6$ alkyl)piperazinyl, or N-aryl-piperazinyl, (g) $C_3$-$C_7$ cycloalkyl;

$R^9$ is
(a) hydrogen,
(b) F, Cl, Br or I,
(c) $C_1$-$C_4$ alkyl,
(d) $C_1$-$C_4$ alkoxy; and $R^{10}$ is
(a) hydrogen,
(b) $C_1$-$C_5$ alkyl,
(c) phenyl.

The term "phenyl" as used herein represents an unsubstituted, mono- or disubstituted benzene ring and the substituent selected from the group: hydroxy, $C_1$-$C_4$ alkoxy, halo (F, Cl, Br or I), $NO_2$, cyano, di($C_1$-$C_4$ alkyl) amino, amino, $CF_3$, $C_1$-$C_4$ alkylthio, P(O)(OH)$_2$, $C_1$-$C_4$ alkyl, —OPO($OC_1$-$C_6$ alkyl)$_2$, —OPO(OH)$_2$, —OCO($CH_2$)$_2$—COOH, $OSO_3H$, —O($C_2$-$C_3$ alkyl-O)$_n$—$C_1$-$C_3$ alkyl, where n=1–3, $C_1$-$C_3$ alkyl, $C_1$-$C_4$ alkylsulfonyl, $C_1$-$C_4$ alkysulfinyl.

The term "heteroaryl" as used herein represents an unsubstituted, monosubstituted or disubstituted five or six membered aromatic ring which contains 1 to 4 heteroatoms selected from O, S, or N wherein one O and/or one S can be present with 0–2N, or O and S are absent and 1–4N are present and the substituents are independently selected from the group consisting of hydroxy, $C_1$-$C_4$ alkoxy, F, Cl, I, Br, $NO_2$, cyano, di($C_1$-$C_4$alkyl)amino, $CF_3$, $C_1$-$C_4$ alkylthio, $C_1$-$C_4$-alkylsulfinyl, —OPO(O-benzyl)$_2$, or $C_1$-$C_4$ alkylsulfonyl, amino, P(O)(OH)$_2$, $C_1$-$C_4$ alkyl, —OPO(O—$C_1$-$C_6$ alkyl)$_2$, OPO(OH)$_2$, OCO($CH_2$)$_2$COOH, $OSO_3H$, or O($C_2$-$C_3$alkyl-O—)n $C_1$-$C_3$ alkyl, where n=1–3. Substitution on the heteroaryl ring is on a ring carbon atom, or can also be on a ring nitrogen atom, providing a tetravalent ammonium cation is not formed.

Representative, heteroaryl rings include: pyridyl, furoyl, pyrrolyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl, and benzoxazolyl.

The terms "alkyl," "alkenyl," "alkynyl," and the like include both the straight chain and branched chain species of these generic terms wherein the number of carbon atoms in the species, as defined, permit. The term "alkenyl" denotes a radical containing one double bond, and "alkynyl", one triple bond. Unless otherwise noted, the specific names for these generic terms shall mean the straight chain species. For example, the term "butyl" shall mean the normal butyl substituent, n-butyl.

One embodiment of this invention is represented by the compounds of the Formula (I) wherein $R^5$ is $CO_2R^7$ and $R^1$ is tetrazol-5-yl, $R^4$ is
a) $C_2$-$C_6$ alkyl,
b) substituted $C_2$-$C_6$ alkyl in which the substituent is: $OC_1$-$C_4$ alkyl, cyclohexyl, phenyl,
c) benzyl,
d) substituted benzyl in which the substituent on the phenyl group is: F, Cl Br, I, OH, $OC_1$-$C_4$ alkyl, $NO_2$, $NH_2$, N($C_1$-$C_4$ alkyl)$_2$,
e) $CH_2$-heteroaryl or
f) $C_3$-$C_6$-alkenyl;

$R^6$ is
a) methyl, ethyl,
b) non-linear substituted $C_1$-$C_6$ alkyl in which the substituent is: -benzyl, —$C_1$-$C_3$ alkyl, or —$OC_1$-$C_4$alkyl, or
c) cyclopropyl;

$R^7$ is
a) $C_1$-$C_6$ alkyl,
b) benzyl,
c) $C_2$-$C_4$ alkyl-O—$C_1$-$C_4$ alkyl.

Illustrating this embodiment are the following compounds (with their Example Number designation) of the Formula (I), wherein "TET" represents tetrazolyl, "iBu, t-Bu" represent isobutyl and t-butyl, respectively, and "Bn" represents benzyl.

TABLE 1

| # | $R^6$ | $R^1$ | $R^7$ | $R^4$ |
|---|---|---|---|---|
| 1 | Et | TET | iBu | Bn |
| 2 | iBu | TET | iBu | Bn |
| 3 | Me | TET | iBu | Bn |
| 4 | Et | TET | t-Bu | Bn |
| 5 | Et | TET | Bn | Bn |

A second embodiment of this invention is represented by the compounds of the Formula (I) wherein $R^5$ is $COR^8$ and $R^1$ is tetrazol-5-yl, $R^4$ is
a) $C_3$-$C_6$ alkyl,
b) substituted $C_3$-$C_6$ alkyl in which the substituent is: $OC_1$-$C_4$ alkyl, cyclohexyl, phenyl,
c) benzyl,
d) substituted benzyl in which the substituent on the phenyl group is: F, Cl Br, I, OH, $NO_2$, $NH_2$, N($C_1$-$C_4$ alkyl)$_2$, O-benzyl, O—$C_1$-$C_4$alkyl, or O-phenyl;
e) $CH_2$-heteroaryl or
f) $C_3$-$C_6$-alkenyl;

$R^6$ is
(a) methyl,
(b) ethyl,
(c) isopropyl,
(d) isobutyl,
(e) 1-ethylpropyl,
(f) $CH_2OMe$,
(g) cyclopropyl,
(h) propyl;

$R^{10}$ is
(a) phenyl,
(b) substituted phenyl in which the substituent is F, Cl, Br, I, methoxy, methyl, $CF_3$, SMe, OH, O-benzyl or $OC_6H_5$,
(c) heteroaryl.

Illustrating this second embodiment are the following compounds (with their Example Number designation) of the Formula (I), wherein in addition to the abbreviations listed above, "cPr" represents cyclopropyl, "Pn" and "iPn" represent pentyl and isopentyl, respectively, and "Pyr" represents pyridyl:

TABLE 2

| Example # | $R^6$ | $R^1$ | $R^8$ | $R^4$ |
|---|---|---|---|---|
| 6 | Pr | TET | Ph-2-OPh | Bn |
| 7 | Pr | TET | Ph-4-OMe | Bn-4-OMe |
| 8 | Pr | TET | Ph-3,4,5-(OMe)₃ | Bn |
| 9 | Pr | TET | Ph-2-OMe | Bn |
| 10 | Pr | TET | Ph | Bn-4-Cl |
| 11 | Pr | TET | Ph-4-N₃ | Bn |
| 12 | Pr | TET | Ph | Bn-2-OMe |
| 13 | Pr | TET | Ph | Bn-3,4-Cl₂ |
| 14 | Pr | TET | Ph | Bn-2-OEt |
| 15 | Pr | TET | Ph | Bn |
| 16 | Pr | TET | Ph-3,4-Cl₂ | Pn |
| 17 | Pr | TET | Ph | Bn-4-Me |
| 18 | Pr | TET | 2-furoyl | Bn |
| 19 | Pr | TET | pyrazinyl | Bn |
| 20 | Et | TET | 2-thiophenyl | CH₂—pyridyl-OH-I (see structure) |
| 21 | Pr | TET | Ph | Bn |
| 22 | Pr | TET | Ph-4-F | Bu |
| 23 | Pr | TET | Ph-4-Me | Pn |
| 24 | Et | TET | Ph | Bn |
| 25 | Et | TET | Ph-4-F | Pn |
| 26 | Et | TET | Ph-4-F | Bu |
| 27 | Et | TET | Ph | Bn-4-F |
| 28 | c-Pr | TET | Ph | Bn |
| 29 | Me | TET | Ph | Bn |
| 30 | iPr | TET | Ph | Bn |
| 31 | Et | TET | 4-Pyr | Bn |
| 32 | Et | TET | Ph-2-Cl | Bn |
| 33 | Et | TET | Ph-2-Cl | Bn-2-Cl |
| 34 | Et | TET | Ph | Bn-2-Cl |
| 35 | Et | TET | Ph | CH₂CH=CMe₂ |
| 36 | Et | TET | Ph | iPn |
| 37 | iPr | TET | Ph | Bn-2-Cl |
| 38 | iPr | TET | cPr | Bn |
| 39 | iPr | TET | cPr | Bn-2-Cl |
| 40 | H | TET | Ph | Bn |
| 41 | Et | TET | Ph | Bn-4-Cl |
| 42 | Et | TET | Ph | Bn-4-F |
| 43 | Et | TET | Ph | Bn-3-Et |
| 44 | 1-methylpropyl | TET | Ph | Bn |
| 45 | 1-methylpropyl | TET | Ph | Bn-2-Cl |
| 46 | Me | TET | 4-Pyr | Bn |
| 47 | Me | TET | 4-Pyr | Bn-2-Cl |
| 48 | Et | TET | Ph | Bn-4-I |
| 49 | iPr | TET | Ph | Bn-4-I |
| 50 | Et | TET | Ph-4-I | Bn |
| 51 | Et | TET | Ph | Bn-2-I |
| 52 | Et | TET | 2-thienyl | Bn |
| 53 | CH₂OMe | TET | Ph-4-Cl | Pn |
| 54 | Pr | TET | 2-thienyl | Bn |
| 55 | Pr | TET | 3-Pyr | Bn |

TABLE 2-continued

| Example # | $R^6$ | $R^1$ | $R^8$ | $R^4$ |
|---|---|---|---|---|
| 56 | Pr | TET | 2-Pyr | Bn |
| 57 | Pr | TET | Ph | CH₂-4-Pyr |
| 58 | Pr | TET | 4-Pyr | Bn |
| 59 | Me | TET | Ph | CH₂-3-Pyr |
| 60 | Me | TET | Ph | CH₂-2-Pyr |

In naming compounds of Formula (I), it should be noted that the following two names for compound (i) shown below are considered to be equivalent:

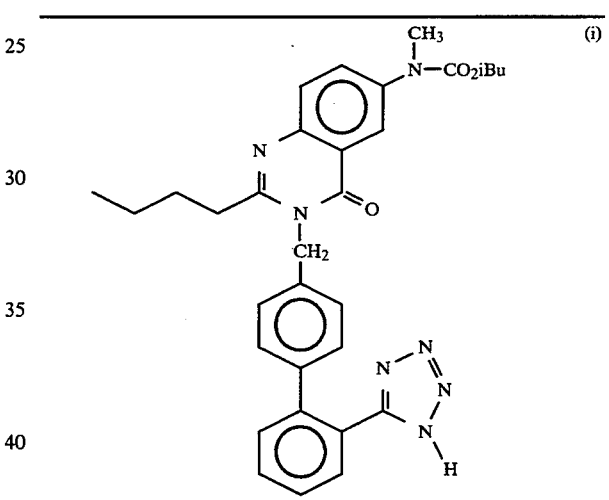

(i)

(1) 2-n-Butyl-6-(N-methyl-N-isobutyloxycarbonyl)-amino-3-[(2'-(tetrazol-5-yl)biphen-4-yl)-methyl]quinazolin-4-(3H)-one; or, (2) 2-n-Butyl-6-(N-methyl-N-isobutyloxycarbonyl)-amino-3-[(2'-(tetrazol-5-yl)[1,1']-biphenyl-4-yl)methyl]-quinazolin-4(3H)-one.

ABBREVIATIONS USED IN SCHEMES

| | |
|---|---|
| DMAP | Dimethylaminopyridine |
| -OTs | p-toluenesulphonate |
| -OTf | Trifluoromethanesulfonate |
| DMF | Dimethylformamide |
| DBU | 1,8-Diazabicyclo[5.4.0]undecane |
| FABMS | Fast Atom bombardment mass spectroscopy |
| THF | Tetrahydrofuran |
| DMSO | Dimethylsulfoxide |
| EtAc | Ethyl acetate |
| HOAc | Acetic Acid |
| TFA | Trifluoroacetic acid. |

Disubstituted 6-aminoquinazolin-4-(1H)-ones of the Formula (I) may be prepaired from 2-cyano-4-nitroaniline (1) as described in Scheme 1. The 2-cyano-4-nitroaniline (1) is acylated using the requisite acyl chloride to give amide (2). The amide (2) is then cyclized with basic hydrogen peroxide to give the appropriately substituted 2-substituted 6-nitroquinazolin-4(3H)-one (3), which is then alkylated using sodium hydride and the appropriate alkyl halide (or pseudohalide)(9). The resulant 2,3-disubstituted 6-nitroquinazolin-4(3H)-one (4) is then reduced to the substituted 6-aminoquinazolin-4(3H)-one (5). The substituted 6-aminoquinazolin-4(3H)-one (5) is then transformed into the desired compounds of the Formula (I) utilizing standard chemical reactions as described below.

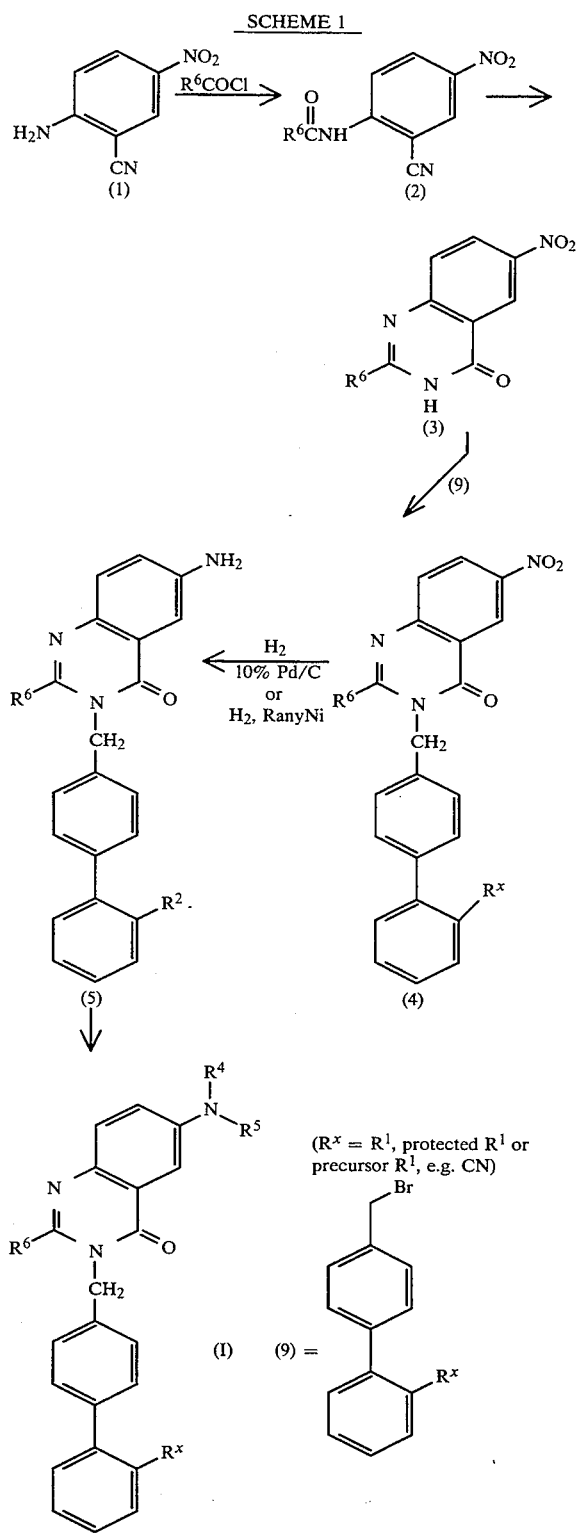

The benzyl halides (9) can be prepared as described in European Patent Applications 253,310 and 291,969 and the references cited therein. However, a preferred method to prepare the biphenyl precursor 8 using Ni(0) or Pd(O) catalyzed cross-coupling reaction [E. Negishi, T. Takahashi, and A. O. King, Org. Synthesis, 66, 67 (1987)] is outlined in Scheme 2. As shown in Scheme 2, treatment of 4-bromotoluene (4a) with t-BuLi, followed by the addition of a solution of $ZnCl_2$, produces the organo-zinc compound (6a). Compound (6a) is then coupled with 7 in the presence of $Ni(PPh_3)_2Cl_2$ catalyst to produce the desired biphenyl compound 8 ($PPh_3$=triphenylphosphine). 8 is then transformed into the halomethylbiphenyl derivative 9 according to procedures described in European Patent Applications 253,310 and 291,969.

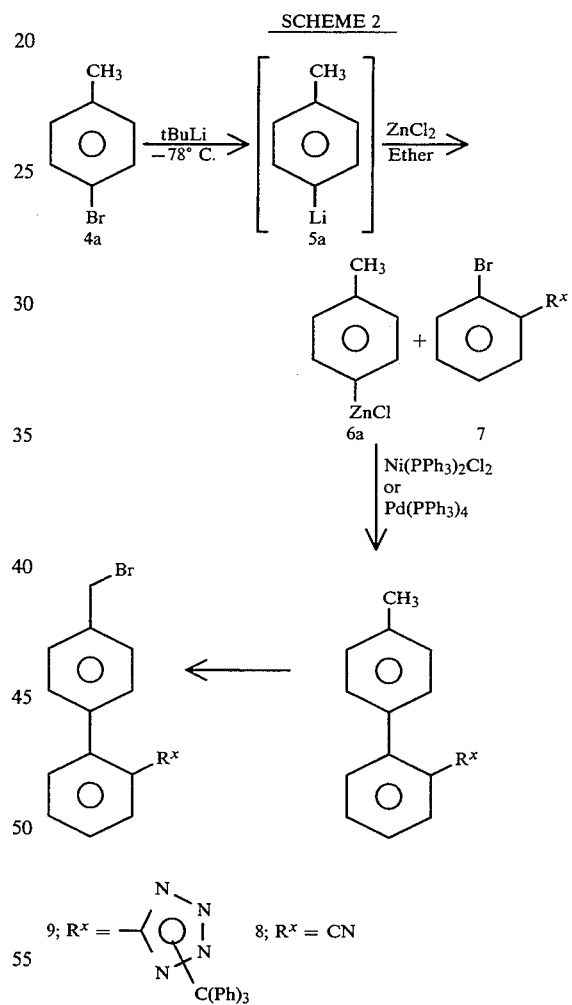

Scheme 3 shows an alternate preparation of 2-substituted 6-nitroquinazolin-4(3H)-ones (3) starting with the corresponding anthranilic acid. The appropriately substituted anthranilic acid (10) is treated with two equivalents of the requisite acyl chloride in DMF with triethylamine and DMAP at 0° C. This is then heated to 110° C. for two hours after which time excess ammonium carbonate is added. [M. T. Bogen, W. F. Hand, J. Am. Chem. Soc. (1906) 28, 94.]

SCHEME 3

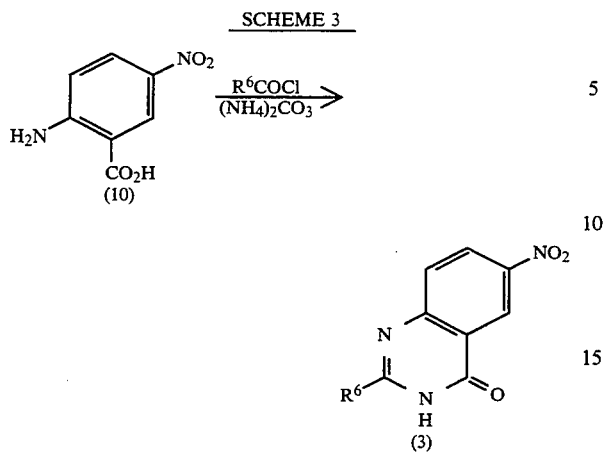

Schemes 4 and Scheme 5 provide an alternate route to compounds of Formula (I).

Two methods, for preparing 1,3,4-benzoxazones (11) are illustrated in Scheme 4. Substituted anthranilic acids (10) may be acylated and cyclized by heating them in DMF with an acyl chloride, triethylamine and DMAP.[A. Khan, R. K. Saksena, *Pharmazie* (1988) 43 H. 12. L. A. Errede, J. J. McBrady, H. T. Oien, *J. Org. Chem.* (1977) 42, 656. L. A. Errede, *J. Org. Chem.* (1976) 41, 1763. L. A. Errede, H. T. Oien, D. R. Yarian, *J. Org. Chem.* (1977) 42, 12. Alternatively, they may also be prepared by heating an appropriately substituted anthranil (12) with an acyl chloride in pyridine. K. Wunsch, A. J. Boulton, *Adv. Het. Chem.* (1967) 8, pp 326–9, and references therein. I. R. Gambhir, S. S. Joshi, *J. Ind. Chem, Soc.* (1964) 41, 47.

SCHEME 4

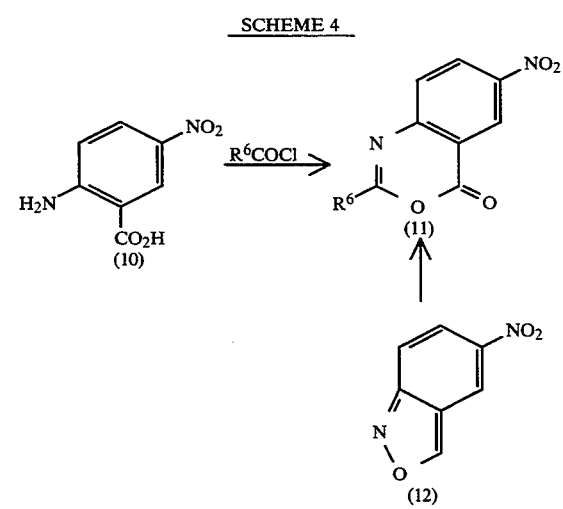

As shown in Scheme 5, the amine (13) and the 1,3,4-benzoxazone (11) are heated together to give the desired 2,3-disubstituted 6-nitroquinazolinone (4). The necessary alkyl amine (13) may be prepared from the alkyl halide (or pseudohalide) (9) using the standard literature procedures. Bayley, Stranding, Knowles, *Tetrahedron. Lett.* (1978) 3633. Rolla, *J. Org. Chem.* (1982) 47, 4327. Gibson, Bradshaw, *Angew, Chem, Int. Ed. Engl.* (1968) 7, 919.

SCHEME 5

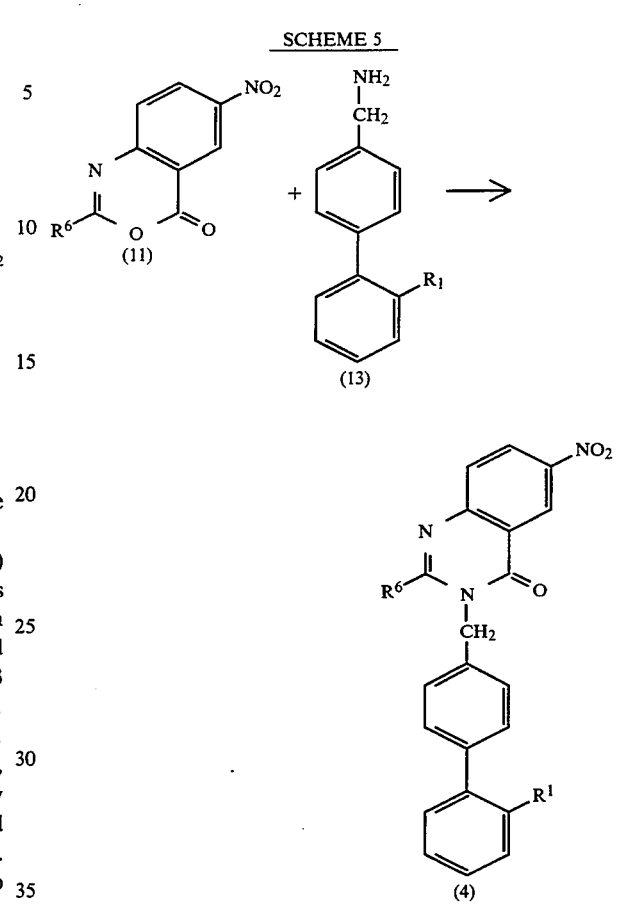

Functionalization of 2,3-disubstituted 6-nitroquinazolinone (4) is accomplished through the following synthetic pathways of Scheme 6, Scheme 7, Scheme 8, Scheme 9 and Scheme 10 and additional routes described in the experimental section. The nitro group is reduced to the substituted 6-aminoquinazolin-4(3H)-one (5) by reduction with hydrogen over palladium on carbon.

To prepare the compounds of the Formula (I) wherein $R^5$ is $CO_2R^7$, the chemical transformations in Scheme 6 are utilized. The acylation of the amine with chloroformates is best carried out in the presence of sodium hydride to form the anilinium anion. This anion reacts quickly with chloroformates to give the carbamates (14). The carbamate may be isolated and then deprotonated with lithium hexamethyldisilazide and alkylated to give the N-alkylated carbamates (15). Alternatively this process may be carried out in one reaction vessel by first preforming the anilinium anion, acylating it and then deprotonating in situ and alkylating to give (15). We have also found that 5 may be acylated with chloroformates under conventional conditions in the presence of $K_2CO_3$.

SCHEME 6

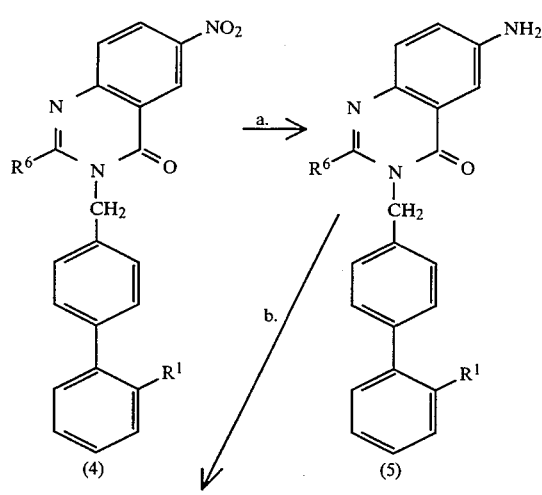

a. $H_2$, 10% Pd/C
b. NaH, $R^7CO_2Cl$
c. $LiN(TMS)_2$, $R^4X$ where X = I, Cl, Br, $OSO_2$ alkyl,
e.g. $-OSO_2CH_3$ or $-OSO_2$ aryl, e.g. $-OSO_2-C_6H_4-p-OCH_3$, or other effective leaving group.

To prepare the compounds of the Formula (I) wherein $R^5$ is $COR^8$, the chemical transformations in Scheme 7 are utilized. The substituted 6-amino-quinazolin-4(3H)-one (5) may be acylated with acid chlorides to give amides (16) under basic conditions. The amide may be isolated and then deprotonated with lithium hexamethyldisilazide and alkylated to give (17). Alternatively, the amide may be similarly alkylated with a suitable alkylating agent $R^4X$, as described above, in the presence of potassium carbonate and sodium hydroxide and a phase transfer catalyst, such as tetrabutyl ammonium hydrogen sulfate.

SCHEME 7

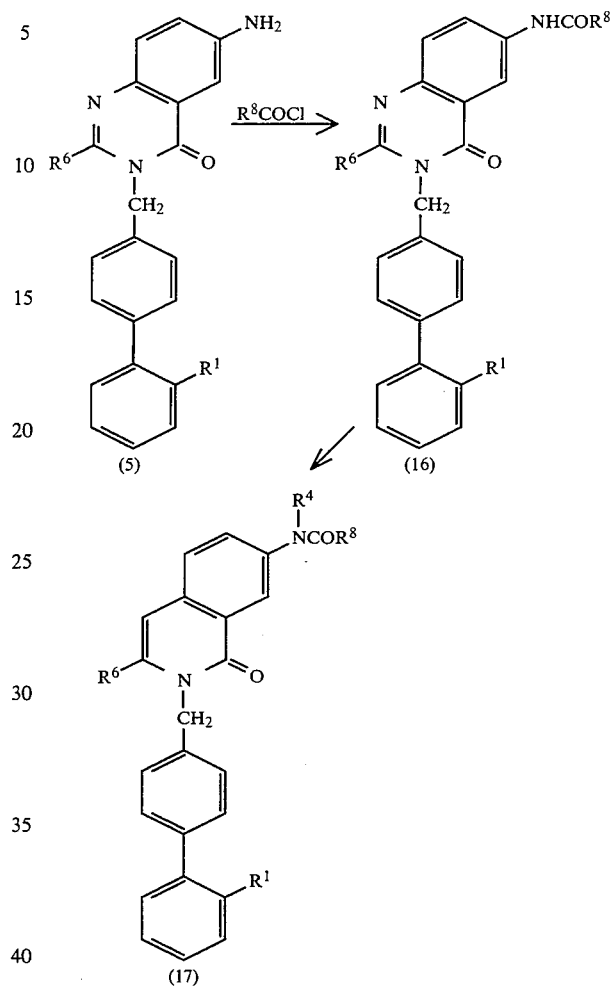

The 6-N-functionalized quinazolinones (21) may be prepared from the 6-nitroquinazolinones (3) as the dimethoxybenzhydryl derivative (18). Reduction of (18) with 10% Pd/C and hydrogen gives amine (19) which is functionalized with $R^4$ and $R^5$ as described in prior Schemes to give (20). The dimethoxybenzhydryl group may be removed by treatment with acid to give (21).

SCHEME 8

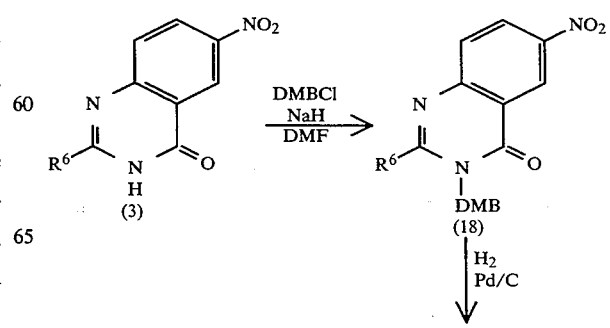

-continued
SCHEME 8

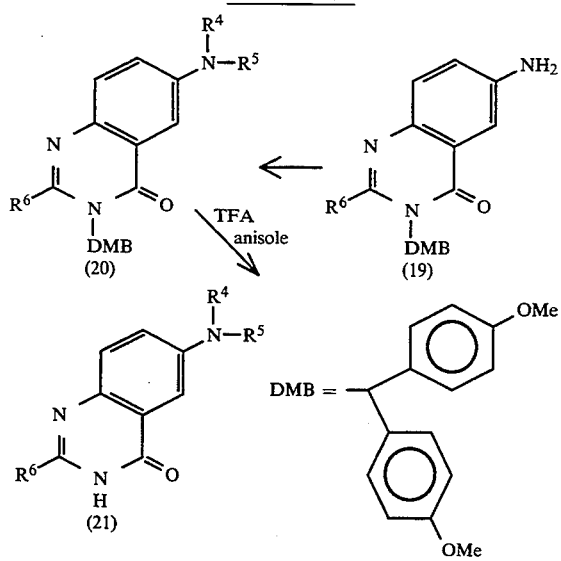

It will be appreciated by those skilled in the art that the protecting groups used in these syntheses will be chosen to be compatible with subsequent reaction conditions. Ultimately, they will be removed to generate the active compounds of formula (I). For example, $R^1$ as carboxyl is often protected as its t-butyl ester which in the last step is removed by treatment with trifluoroacetic acid. Aqueous acetic acid employed overnight or MeOH/HCl is a preferred method to remove a trityl protecting group to liberate an $R^1$ tetrazole group.

The compounds of this invention form salts with various inorganic and organic acids and bases which are also within the scope of the invention. Such salts include ammonium salts, alkai metal salts like sodium and potassium salts, alkaline earth metal salts like the calcium and magnesium salts, salts with organic bases; e.g., dicyclohexylamine salts, N-methyl-D-glucosamine, salts with amino acids like arginine, lysine, and the like. Also, salts with organic and inorganic acids may be prepared; e.g., HCl, HBr, $H_2SO_4$, $H_3PO_4$, methanesulfonic, toluenesulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with $AT_1$ and $AT_2$ receptors present on cell membranes. The compounds described in the present invention act as competitive antagonists of AII at the $AT_2$ receptor. In order to identify AII antagonists and determine their efficacy in vitro, the following two ligand-receptor binding assays were established to determine the relative binding efficiency to the $AT_1$ and $AT_2$ receptors.
Receptor binding assay using rabbit aortae membrane preparation: ($AT_1$ binding efficiency)

Three frozen rabbit aortae (obtained from Pel-Freeze Biologicals) were suspended in 5 mM Tris-0.25M Sucrose, pH 7.4 buffer (50 ml) homogenized, and then centifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/ml Bacitracin and the suspension was used for 100 assay tubes. Samples tested for screening were done in duplicate. To the membrane preparation (0.25 ml) there was added $^{125}$I-Sar$^1$Ile$^8$-angiotensin II [obtained from New England Nuclear] (10 ml; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^{125}$I-Sar$^1$Ile$^8$-angiotensin II was presented as a measure of the efficacy of such compounds as AII antagonists.
Receptor assay using rat brain membrane preparation ($AT_2$ binding efficiency)

Membranes from rat brain (thalamus, hypothalamus and midbrain) were prepared by homogenization in 50 mM Tris HCl (pH 7.4), and centrifuged at 50,000×g. The resulting pellets were washed twice in 100 mM NaCl, 5 mM $Na_2$.EDTA, 10 mM $Na_2HPO_4$ (pH 7.4) and 0.1 mM PMSF by resuspension and centrifugation. For binding assays, the pellets were resuspended in 160 volumes of binding assay buffer (100 mM NaCl, 10 mM $Na_2HPO_4$, 5 mM $Na_2$.EDTA, pH 7.4, 0.1 mM PMSF, 0.2 mg/ml soybean trypsin inhibitor, 0.018 mg/ml o-phenanthroline, 77 mg/ml dithiothreitol and 0.14 mg/ml bacitracin. For $^{125}$I-Sar$^1$Ile$^8$-angiotensin II binding assays, 10 μl of solvent (for total binding), $^{125}$ISar$^1$Ile$^8$-angiotensin II (1 mM) (for nonspecific binding) or test compounds (for displacemere) and 10 μl of [$^{125}$I]-Sar$^1$Ile$^8$-angiotensin II (23–46 pM) were added to duplicate tubes. The receptor membrane preparation (500 μl) was added to each tube to initiate the binding reaction. The reaction mixtures were incubated at 37° C. for 90 minutes. The reaction was then terminated by filtration under reduced pressure through glass-fiber GF/B filters and washed immediately 4 times with 4 ml of 5 mM ice-cold Tris HCl (pH 7.6) containing 0.15M NaCl. The radioactivity trapped on the filters was counted using a gamma counter.

The efficacy of $AT_2$ antagonists at mediating restenosis was evaluated for Compound II, i.e., 2-ethyl-6-(N-benzyl-N-(2-thiophenecarbonyl)amino-3-[(2'-(tetrazol-5-yl)-biphen-4-yl-methyl]quinazolin-4(3H)-one (Example 52). Compound I, an $AT_1$ antagonist, i.e., 5,7-dimethyl-2-ethyl-3-[(2'-(1H-tetrazol-5-yl)[1,1']-biphenyl-4-yl]-methyl]-3H-imidazo[4,5-b]pyridine, described in J. Pharmacology and Experimental Therapeutics, Vol. 262, page 133, 1992, was also tested for comparison.
The effects of the angiotensin II (Site II) receptor antagonist Compound II on restenosis in the rat model A vehicle treatment group was compared to rats treated with: i) the AII ($AT_2$) receptor antagonist, Compound II; ii) Compound II plus the AII ($AT_1$) receptor antagonist, Compound I; iii) Compound II+-heparin; and iv) heparin only. Combination treatment with Compound II and Compound I were administered for the 48 hour period prior to surgery as well as on the day of surgery at 1 mg/kg/day by bolus i.v. Compound II and Compound I treatment was continued at the time of angioplasty at 1 mg/kg/day by continuous i.v. delivery via Alzet minipumps for the duration of the experiments (14 days). Heparin was delivered as a 0.3 mg/kg i.v. bolus at the time of angioplasty followed by continous i.v. delivery at 0.3 mg/kg/hr by Alzet minipump. Heparin treatment was discontinued 4 days later. Fourteen days after balloon angioplasty, the rats were sacrificed and the extent of restenosis was determined by morphometric measurements of the newly-formed intima.

The data below indicates that monotherapy with Compound II inhibited restenosis by 53%. Treatment with the combination of Compound II and Compound I or Compound II+heparin resulted in 41 and 32% inhibition of restenosis, respectively. Heparin treatment alone resulted in 23% inhibition of restenosis.

| Treatment | n | Intimal Area (mm²) | % Inhibition |
|---|---|---|---|
| Control | 8 | 0.205 ± 0.011 | — |
| Compound II | 7 | 0.097 ± 0.027* | 53 |
| Compound II + Compound I | 5 | 0.121 ± 0.013* | 41 |
| Compound II + Heparin | 7 | 0.139 ± 0.017* | 33 |
| Heparin | 8 | 0.158 ± 0.016 | 23 |

*p < 0.05 vs. control, 1-way ANOVA with Dunnett's Multiple Comparison Test

This experiment indicates that administration of compound II alone has a significant effect upon neointimal formation in the rat carotid model.

The Effect of Compound II on restenosis in the rat

Rats were pretreated with Compound II or Compound I for the 48 hour period prior to surgery as well as on the day of surgery (1 mg/kg/day, bolus i.v.). Drug treatment was continued at the time of angioplasty (1 mg/kg/day, continuous i.v.) for the duration of the experiments (14 days).

| Treatment | n | Intimal Area (mm²) | % Inhibition |
|---|---|---|---|
| control | 8 | 0.205 ± 0.011 | — |
| Compound I | 7 | 0.121 ± 0.012* | 41 |
| Compound II | 7 | 0.097 ± 0.027* | 53 |

*p ≤ 0.05 vs. control, 1-way ANOVA with Dunnett's Multiple Comparison Test

The above data alone indicates that either the $AT_1$ or the $AT_2$ receptor antagonist (compound I or II) may independently inhibit growth of the neointimal formation.

The effect of Compound I on restenosis in the Rat: Dose-response study

Compound I was delivered as an i.v. bolus at the time of angioplasty (0.1–1.0 mg/kg) followed by continuous i.v. infusion (0.1–1.0 mg/kg/day) until sacrifice on day 14.

| Compound I (mg/kg/day) | n | Area (mm²) | | |
|---|---|---|---|---|
| | | Intima | Media | I/M |
| 0 | 7 | 0.201 ± 0.016 | 0.125 ± 0.008 | 1.63 ± 0.12 |
| 0.1 | 4 | 0.212 ± 0.013 | 0.129 ± 0.003 | 1.64 ± 0.09 |
| 0.3 | 8 | 0.148 ± 0.014* | 0.103 ± 0.009 | 1.47 ± 0.19 |
| 1.0 | 9 | 0.149 ± 0.009* | 1.121 ± 0.005 | 1.24 ± 0.04* |

*p ≤ 0.05, 1-way ANOVA with Trend Analysis

The data above indicates that compound II inhibits neointimal formation in a dose dependent manner.

The effect of AII+Compound I on restenosis in the rat

AII was delivered by continuous i.v. infusion (14 ug/kg/hr) beginning at the time of angioplasty. Compound I was delivered as an i.v. bolus at the time of angioplasty (1.0 mg/kg) followed by continuous i.v. infusion (1.0 mg/kg/day). Rats were sacrificed on day 14.

| Treatment | n | Area (mm²) | | |
|---|---|---|---|---|
| | | Intima | Media | I/M |
| saline | 6 | 0.194 ± 0.019 | 0.147 ± 0.006 | 1.32 ± 0.12 |
| AII | 5 | 0.348 ± 0.047* | 0.176 ± 0.008* | 1.92 ± 0.19 |
| AII + Compound I | 5 | 0.187 ± 0.035 | 0.145 ± 0.007 | 1.29 ± 0.19 |

*p ≤ 0.05, 1-way ANOVA with Dunnett's Multiple Comparison Test

The data above indicates that the presence of exogenous angiotensin II stimulates the formation of the neointima by almost two fold; and that co-administration of compound I inhibits this stimulation.

The effect of Compound I pretreatment and Compound I—Heparin Combination therapy on restenosis in the rat Compound I was delivered as an i.v. bolus at the time of angioplasty (1.0 mg/kg) followed by continuous i.v. infusion (1.0 mg/kg/day). Some groups were pretreated with Compound I. Pretreatment (PreRx) was begun 48 hr (1 mg/kg/day, i.v. bolus) prior to angioplasty. In all cases, Compound I treatment was continued for 14 days post-angioplasty. Other groups received Compound I in conjunction with heparin (0.3 mg/kg i.v. bolus+0.3 mg/kg/hr continuous i.v.) begun at the time of angioplasty and discontinued either 2 or 4 days later. The Hep 4d and Hep 2d data from above is included.

| Treatment | n | Area (mm²) | | |
|---|---|---|---|---|
| | | Intima[1] | Media | I/M |
| Control | 10 | 0.196 ± 0.019 | 0.144 ± 0.008 | 1.33 ± 0.07 |
| Cmpd. I | 9 | 0.149 ± 0.009 | 0.125 ± 0.006 | 1.19 ± 0.04 |
| Cmpd. I PreRx | 10 | 0.125 ± 0.010 | 0.124 ± 0.006 | 1.01 ± 0.07 |
| Cmpd. I + Hep 4d | 8 | 0.095 ± 0.019 | 0.119 ± 0.008 | 0.78 ± 0.15 |
| Cmpd. I PreRx + Hep 2d | 8 | 0.108 ± 0.008 | 0.107 ± 0.007 | 1.01 ± 0.08 |
| Cmpd. I PreRx + Hep 4d | 8 | 0.074 ± 0.011 | 0.117 ± 0.008 | 0.66 ± 0.12 |
| Hep 4d | 8 | 0.158 ± 0.016 | 0.136 ± 0.010 | 1.17 ± 0.10 |
| Hep 2d | 8 | 0.144 ± 0.012 | 0.130 ± 0.008 | 1.14 ± 0.13 |

[1]average ± sem, all treatment groups except Hep 4d were significantly different (p ≤ 0.05) from the control groups (1-way ANOVA with Dunnett's Multiple Comparison Test).

The data above indicates that pretreatment of the animal for 2 days prior to the procedure resulted in a reduction in the neointimal area when compared with no pretreatment and that the co-administration of heparin with compound I in each case resulted in a greater degree of reduction in the neointimal area compared with treatment with compound I alone.

The effect of Heparin on restenosis in the rat: time course

Heparin (0.3 mg/kg/hr) was delivered by i.v. bolus (0.3 mg/kg) at the time of angioplasty followed by continuous i.v. delivery for 2, 4 or 14 days (0.3 mg/kg,hr). The animals were sacrificed on day 14.

| Heparin Treatment (days) | n | Area (mm²) | | |
|---|---|---|---|---|
| | | Intima | Media | I/M |
| 0 | 9 | 0.198 ± 0.021 | 0.144 ± 0.009 | 1.35 ± 0.09 |
| 2 | 8 | 0.144 ± 0.012* | 0.130 ± 0.008 | 1.14 ± 0.13 |
| 4 | 8 | 0.158 ± 0.016 | 0.136 ± 0.010 | 1.17 ± 0.10 |
| 14 | 11 | 0.098 ± 0.008* | 0.128 ± 0.004 | 0.77 ± 0.05* |

*$p \leq 0.05$, 1-way ANOVA with Trend Analysis

The data above indicates that heparin alone decreases the formation of neointima and that greatest degree of inhibition was observed when heparin was given for 14 days.

AII Receptor Antagonist: The effect of enalaprilat, the AII (site 2) receptor antagonist, Compound II, and Compound II in combination with the AII (site 1) receptor antagonist, Compound I, were evaluated in the rat carotid artery model of balloon angioplasty. Rats were pretreated surgery and drag treatment was continued (1 mg/kg/day, continuous i.v.) by ALZET minipump for the duration of the experiments. Fourteen days after balloon angioplasty, the rats were sacrificed and the extent of restenosis was determined by morphometric measurements of the newly-formed intima. The results below indicate that enalaprilat and Compound II inhibit restenosis in this model.

| Treatment | n | Intimal Area + sem (mm²) | % Inhibition |
|---|---|---|---|
| control | 8 | 0.205 ± 0.011 | — |
| I pt | 7 | 0.121 ± 0.012* | 41 |
| II pt | 7 | 0.097 ± 0.027* | 53 |
| II pt + I pt | 5 | 0.121 ± 0.013* | 41 |
| enalaprilat | 7 | 0.133 ± 0.016* | 35 |

*$p \leq 0.05$ vs. vehicle, Duncan's multiple range test

"The results above indicate that with pretreatment, compounds I, II, and enalaprilat independently inhibit neointima in this model."

In the treatment of the clinical conditions noted above, the compounds of this invention may be utilized in compositions such as tablets, capsules or elixirs for oral administration, suppositories for rectal administration, sterile solutions or suspension for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severily of disease, the patient's weight, special diets then being followed by a patient, concurrent medication, and other factors which those skilled in the art will recognize, the dosage range will generally be about 5 to 6000 mg. per patient per day which can be administered in single or multiple doses. Preferably, the dosage range will be about 10 to 4000 mg. per patient per day; more preferably about 20 to 2000 mg. particularly in the range of from about 0.1 mg/kg to about 100 mg/kg per patient per day.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carder such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable, oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of formula (I) and their incorporation into pharmaceutical compositions and as such are not to be considered as limiting the invention set forth in the claims appended hereto. All $^1$H-NMR spectra were recorded on a Varian XL-400 Fourier transform spectrometer. Chemical shifts are reported as (parts per million) downfield from tetramethyl silane. Mass spectra were obtained from the Merck and Co. mass spectral facility in Rahway, N.J. Analytical TLC was conducted on E. M. Merck precoated silica plates (0.25 mm in glass, Kieselgel 60 $F_{254}$) with UV visualization. All chromatography was conducted on E. M. Merck silica gel. All reactions were carried out under an atmosphere of dry nitrogen under standard conditions for those skilled in the art.

The representative compounds of the Formula (I) as tabulated below have been prepared utilizing the following general and specific procedures.

PREPARATION OF QUINAZOLINONE HETEROCYCLES

6-nitro-2-propyl-quinazolin-4(1H)-one

To a suspension of 48.94 g (0.3 mol) of 3-nitro-5-amino-benzonitrile in 500 ml of $CH_2Cl_2$ was added 63 ml of $Et_3N$, 3 g DMAP and lastly, dropwise, 45.5 g (0.45 mol) of butyryl chloride. A mild exothermic reaction ensued. The mixture was allowed to stir for 2 days (monitor TLC with 50% EtOAc/hexanes). The solution was washed with 1N HCl ($2 \times 100$ ml), water ($1 \times 100$ ml) sat. $NaHCO_3$ ($2 \times 100$ ml), brine ($1 \times 100$ ml) and dried over $MgSO_4$. The suspension was filtered and concentrated in vacuo. The residue was suspended in a mixture of 600 ml of MeOH and 200 ml of water in a three neck round bottom flask. To this was added gradually 140 ml (0.7 m) of 5N NaOH solution followed by the dropwise addition of 80 ml of 30% $H_2O_2$ (0.7 mol) solution (beware of exothermic reaction!). The mixture was refluxed over night, cooled to room temperature and filtered. The filtrate was acidified with 1N HCl cooled to 5° C. and filtered. The quinazolinone may be recrystallized form hot MeOH to give 38 g of pale brown free crystals. 54% yield. $^1$H-NMR-CDCl$_3$: 1.10 (t, 3H, J=7.8 Hz), 1.93 (m, 2H), 2.79 (t, 2H, J=7.3 Hz), 7.81 (d, 1H, J=8.9 Hz), 8.55 (dd, 1H, J=2.4, 8.8 Hz), 9.14 (d, 1H, J=2.4 Hz), 10.72 (bs, 1H).

The following quinazolinones were prepared in the same manner as described above by using the appropriate acyl chloride:

2-ethyl-6-nitro-quinazolin-4(3H)-one $^1$H-NMR (CD$_3$OD/CDCl$_3$-200 MHz): 1.35(t,3H. J=7.6 Hz), 2.70 (q, 2H, J=7.6 Hz), 7.74 (d, 1H ,. J=9.2 Hz), 8.48 (dd, 1H, J=9.2, J=2.8 Hz), 9.01(d, 1H, J=2.8 Hz).

2-methyl-6-nitro-quinazolin-4(3H)-one $^1$H-NMR (CDCl$_3$): 2.73 (s, 3H), 7.86 (d, 1H, J=9.0 Hz), 8.74 (dd, 1H, J=2.7, 9.0 Hz), 9.03 (d, 1H, J=2.7 Hz).

2-methoxymethyl-6-nitro-quinazolin-4(3H)-one

To a suspension of 13 g (0.08M) of 5-nitroanthranilonitrile in 100 ml of CH$_2$Cl$_2$ and 17 ml (0.12M) of triethyl amine and a catalytic quantity of DMAP was added 8.05 ml (0.88M) of methoxyacetyl chloride dropwise. The reaction was exothermic and was stirred over night at room temperature. The suspension was diluted with 100 ml of CH$_2$Cl$_2$ and washed with 1N HCl (3×30 ml), water (1×30 ml) and brine (1×50 ml) and the resulting solution was dried over MgSO$_4$, filtered and concentrated in vacuo to give 18.0 g of a yellow solid. To 10 g (0.042M) of this solid in 100 ml of MeOH was added 12.4 ml (0.062M) of 5M NaOH solution followed by the slow addition of 7.07 ml (0.062M) of 30% H$_2$O$_2$ in water. The reaction mixture was heated to reflux over night to give a suspension. The reaction mixture was filtered and the filtrate was acidified to give a yellow solid: 2.57 g. 35% yield. 200 MHz-$^1$H-NMR (CDCl$_3$):3.58 (s, 3H), 4.52 (s, 2H), 7.46 (d, 1H, J=8.9 Hz), 8.54 (dd, 1H, J=2.6, 8.9 Hz), 9.14 (d, 1H, J=2.6 Hz), 9.90 (bs, 1H).

Preparation of 3-Alkylated Quinazolinones

6-Nitro-2-n-propyl-3-[(2'-(N-triphenylmethyl-tetrazol-5-yl)-biphen-4-yl)-methyl]quinazolin-4(3H)-one To a suspension of 1.8 g (0.059 m) of 80% NaH in 150 ml of dry DMF at 0° C. under N$_2$ was added 12.64 g (0.054 m) of the 2-propyl-6-nitro quinazolinone as a solid portionwise. The resulting mixture gradually dissolved with evolution of H$_2$. To the resulting solution was added 40.7 g (0.059 m) of N-triphenylmethyl-5-[2-(4'-bromomethylbiphenyl)]tetrazole in 200 ml of dry DMF (10 min). The reaction mixture was allowed to warm to room temperature overnight. The TLC (50% EtAc/hexanes) indicates the formation of two products, a less polar O-alkylated product and more polar N-alkylated material. The reaction mixture was poured into 1300 ml of 0.1N NaOH (this removed any unreacted quinazolinone). The resulting yellow solid was recovered by filtration and then redissolved in CH$_2$Cl$_2$, washed with brine and dried over MgSO$_4$. The solution was filtered and concentrated in vacuo. The residue was purified by trituration with 50% EtOAc/hexanes. The unreacted bromide and O-alkylated products dissolve preferentially in the organic phase leaving the desired product as a solid. Recovered 32 g of a brown/grey solid.

2-ethyl-3-[(2'-(N-triphenylmethyl-tetrazol-5-yl)biphen-4-yl)-methyl]-6-nitroquinazolin-4(3H)-one 2-ethyl-6-nitro-quinazolin-4(1H)-one was alkylated with N-triphenylmethyl-5-[2-(4'-bromomethylbiphenyl)]tetrazole in the same general manner as above. The product was purified by flash chromatography over silica gel. (CDCl$_3$-300 MHz): 1.28, (t, 3H, J=7.2 Hz), 2.72, (q, 2H, J=7.2 Hz), 5.32, (br.s, 2H), 6.89-7.01, (m, 8H), 7.13, (d, 2H, J=8.1 Hz), 7.21-7.38, (m, 10H), 7.45-7.55, (m, 2H), 7.81, (d, 1H, J=9.0, Hz), 7.98, (dd, 1H, J=8.0 Hz, J=2.4 Hz), 8.56, (dd, 1H, J=9.0 Hz, J=2.7, Hz), 9.21, (d, 1H, J=2.7 Hz).

2-methyl-3-[(2'-(N-triphenylmethyl-tetrazol-5-yl)biphen-4-yl)-methyl]-6-nitroquinazolin-4(3H)-one 2-methyl-6-nitro-quinazolin-4(1H)-one was alkylated with N-triphenylmethyl-5-[2-(4'-bromomethylbiphenyl)]tetrazole in the same general manner as above. The product was purified by trituration with 10% EtOAc/hexanes to give a 60% yield of the title compound. (CDCl$_3$-300 MHz):

2-methoxymethyl-3-[(2'-(N-triphenylmethyl-tetrazol-5-yl)-biphen-4-yl)-methyl]-6-nitroquinazolin-4(3H)-one 2-methoxymethylquinazolin-4(3H)-one was alkylated in the same manner as described above for 6-nitro-2-n-propyl-3-[(2'-(N-triphenylmethyl-tetrazol-5-yl)-biphen-4-yl)-methyl]-quinazolin-4(3H)-one to give the title compound. 200 MHz-$^1$H-NMR (CDCl$_3$): 3.43 (s, 3H), 4.36 (s, 2H), 5.46 (bs, 2H), 6.90 (m, 6H), 7.00 (d, 2H J=8.2 Hz), 7.12 (d, 2H, J=8.2H), 7.19-7.38 (m, 10H), 7.48 (m, 2H), 7.84(d, 1H, J=8.9 Hz), 7.92 (m, 1H), 8.56 (dd, 1H, J=2.7, 9.01 Hz), 9.20 (d, 1H, J=2.6 Hz).

2-isopropyl-3-[(2'-(N-triphenylmethyl-tetrazol-5-yl)biphen-4-yl)-methyl]-6-nitroquinazolin-4(3H)-one To the solution of 2-isopropyl-3-[(2'-(N-triphenylmethyl-tetrazol-5-yl)-biphen-4-yl)-methyl]-6-nitro quinazolin-4(3H)-one (85 mg, 0.12 mmol) in methylene chloride.(4 ml) were added (n-Bu)$_4$NBr (20 mg), methyl iodide (0.5 ml) and 50% aq. NaOH (1.0 ml) and the reaction mixture was stirred vigorously for 72 hrs at room temp. After diluting with water the organic layer was separated, evaporated in vacuo and the glassy residue was chromatographed on Chromatotron plate (hexane/AcOEt-2/1) to furnish the title product as yellow glass. 200 MHz-$^1$H-NMR (CDCl$_3$): 1.24 (d, 6H, J=7.2 Hz), 3.08(sept., 1H, J=7.2 Hz), 5.36(m, 2H), 6.88-7.01(m, 8H), 7.12(d, 2H, J=8.0 Hz), 7.20-7.52(m, 12H), 7.77(d, 1H, J=8.8 Hz), 7.86-7.93(m, 2H), 8.52(dd, 1H, J=8.8, J=2.6 Hz), 9.16(d, 1H, J=2.6 Hz).

Preparation of 6-Amino Quinazolinones

6- Amino-2-n-propyl-3-[(2'-(N-triphenylmethyl-tetrazol-5-yl)-biphen-4-yl)-methyl]-quinazolin-4(3H)-one 6-Nitro-2-n-propyl-3-[(2'-(N-triphenylmethyl-tetrazol-5-yl)-biphen-4-yl)-methyl]-quinazolin-4(3H)-one was hydrogenated as described above. The product was purified by flash chromatography over silica gel eluting with 7% acetone/CH$_2$Cl$_2$ to give a pale yellow solid. 72% yield.

$^1$H-NMR (CDCl$_3$): 0.92 (m, 3H, J=7.7 Hz), 1.72 (m, 2H), 2.58 (3 line m, 2H, J=7.7 Hz), 5.56 (bs, 2H), 6.82-7.51 (m, 25H), 7.92 (dd, 1H, J=6.9, 1.9 Hz).

6-Amino-2-ethyl-3-[(2'-(N-triphenylmethyl-tetrazol-5-yl)-biphen-4-yl)-methyl]-quinazolin-4(3H)-one 6-Nitro-2-ethyl-3-[(2'-(N-triphenylmethyltetrazol-5-yl)-biphen-4-yl)-methyl]-quinazolin-4(3H)-one (0.11 g) was hydrogenated in dioxane (2.0 ml) solution under 1 atm H$_2$ for 1 hr in the presence of Raney nickel catalyst.

6-Amino-2-methyl-3-[(2'-(N-triphenylmethyl-tetrazol-5-yl)-biphen-4-yl)-methyl]-quinazolin-4(3H)-one 6-Nitro-2-methyl-3-[(2'-(N-triphenylmethyltetrazol-5-yl)-biphen-4-yl)-methyl]-quinazolin-4(3H)-one was hydrogenated as described above. The product was purified by flash chromatography over silica gel eluting with 6% acetone/CH$_2$Cl$_2$ to give a pale yellow solid. 42% yield. $^1$H-NMR (CDCl$_3$-200 MHz): 2.34 (s, 3H), 3.95 (bs, 2H), 5.25 (bs, 2H), 6.82-7.53 (m, 17H), 7.95 (m, 1H).

6-Amino-2-methoxymethyl-3-[(2'-(N-triphenylmethyl-tetrazol-5-yl)-biphen-4-yl)-methyl]-quinazolin-4(3H)-one 2-methoxymethyl-3-[(2'-(N-triphenylmethyltetrazol-5-yl)-biphen-4-yl)-methyl]-6-nitroquinazolin-4(3H)-one was hydrogenated as described above. The product was purified by flash chromatography over silica gel eluting with 2% MeOH/CH$_2$Cl$_2$ to give a pale yellow solid. $^1$H-NMR (CDCl$_3$): 3.39 (s, 3H), 3.71 (s, 2H), 4.30 (s, 2H), 5.55 (bs, 2H), 6.89–7.51 (m, 24H), 7.55 (d, 1H, J=14 Hz), 7.91 (m, 1H).

6-Amino-2-isopropyl-3-[(2'-(N-triphenylmethyl-tetrazol-5-yl)-biphen-4-yl)-methyl]-quinazolin-4(3H)-one 6-Nitro-2-isopropyl-3-[(2'-(N-triphenylmethyl-tetrazol-5-yl)-biphen-4-yl)-methyl]-quinazolin-4-(3H)-one was hydrogenated overnight at 1 atm H$_2$ in dioxane solution in presence of Raney nickel catalyst as described above. The product was purified by flash chromatography over silica gel eluting with CH$_2$Cl$_2$/MeOH-20/1 to give a pale yellow solid. $^1$H-NMR (CDCl$_3$): 1.20, (d, 6H, J=6.4 Hz), 2.89–3.06, (m, 1H), 5.34, (br.s, 2H), 6.85–7.68, (m, 24H), 7.84–7.92, (m, 1H).

Preparation of 6-Amino-3-(4,4'-dimethoxybenzhydryl)-2-propyl-quinazolin-4(3H)-one Step 1

3-(4,4'-Dimethoxybenzhydryl)-2-propyl-6-nitro-quinazolin-4(3H)-one

To a suspension of 10.0 g (45 mmol) of 2-propyl-6-nitro-quinazolin-4(3H)-one in 160 ml of dry CH$_2$Cl$_2$ was added 9.5 ml (67 mmol) of triethylamine followed by 12.9 g (49 mmol) of 4,4'-dimethoxybenzhydryl chloride. The reaction mixture was stirred for 48 hours and then washed with 10% citric acid (2×20 ml), water (1×20 ml), saturated NaHCO$_3$ (2×20 ml) and brine (1×20 ml). The solution was dried over MgSO$_4$, filtered and concentrated in vacuo. The residue was recrystalised from EtOAc to give 17.3 g of white solid. 85% yield. $^1$H-NMR (CDCl$_3$): 0.87 (t, 3H, J=7.3 Hz), 1.58 (bm, 2H), 2.72 (t, 2H, J=7.8 Hz), 3.80 (s, 6H), 6.88 (d, 4H, J=9 Hz), 7.19 (d, 4H, J=9.0 Hz), 7.73 (d, 1H, J=8.9 Hz), 8.48 (dd, 1H, J=2.8, 9.0 Hz), 9.08 (d, 1H, J=2.8 Hz).

Step 2

6-Amino-3-(4,4'-dimethoxybenzhydryl)-2-propyl-quinazolin-4(3H)-one

A solution of 12.1 g (26.0 mmol) of 3-(4,4'-dimethoxybenzhydryl)-2-propyl-6-nitro-quinazolin-4-(3H)-one dissolved in 250 ml of EtOAc was hydrogenated under atmospheric pressure over three days in the presence of three portions of 1.2 g of 10% Pd/C added daily. The mixture was filtered through celite and concentrated in vacuo to give an oil. The product was purified by flash chromatography over silica gel eluting with 50% EtOAc/hexanes to give 7.8 g (18.7 mmol) of the amine. 72% yield. $^1$H-NMR (CDCl$_3$):0.82 (t, 3H, J=7.2 Hz), 1.49 (bm, 2H), 2.61 (t, 2H, J=7.81 Hz), 3.79 (s, 6H), 3.90 (bs, 2H), 6.85 (d, 4H, J=8.8 Hz), 7.08 (dd, 1H, J=2.8, 8.7 Hz), 7.20 (d, 4H, J=8.4 Hz), 7.42 (d, 1H, J=2.7 Hz), 7.47 (d, 1H, J=8.7 Hz).

General Procedure For The Deprotection Of The Tetrazole

The triphenyl methyl group was removed by dissolving for example, the C-6 derivatized quinazolinone (0.2 g) in MeOH (5 ml) in the presence of several drops (3–5) of concentrated hydrochloric acid. After 2 hours at room temperature a few crystals of phenopthalien were added and the reaction mixture was made basic by addition of 5N NaOH solution. The reaction mixture was reacidified by addition of acetic acid and then concentrated in vacuo. The residue was dissolved in 20 ml of EtOAc and washed with water (3×5 ml) and brine (1×5 ml) and dried over MgSO$_4$. The mixture was filtered and concentrated in vacuo and the residue was purified by flash chromatography over silica gel.

Alternatively, the triphenyl methyl group could be removed by stirring overnight in a solution of 3:1:1 acetic acid:water:THF, concentrating in vacuo and purifiying the residue with a solvent mixture of suitable polarity (usually EtOAc/hexanes/1% acetic acid).

Described below are various general synthetic routes that were followed to prepare the compounds that are detailed in Table 1.

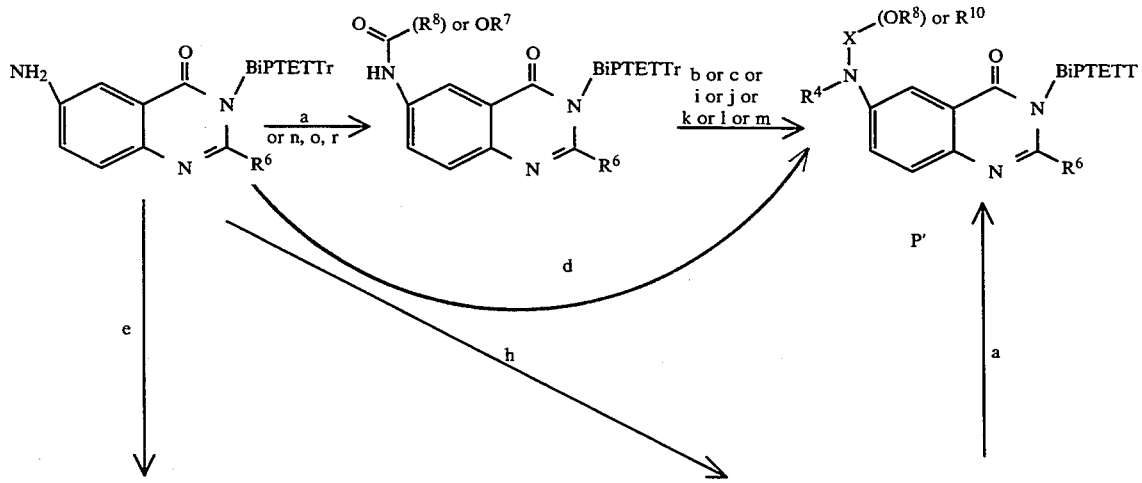

General Synthetic Routes to 6-Substituted Amino Compounds

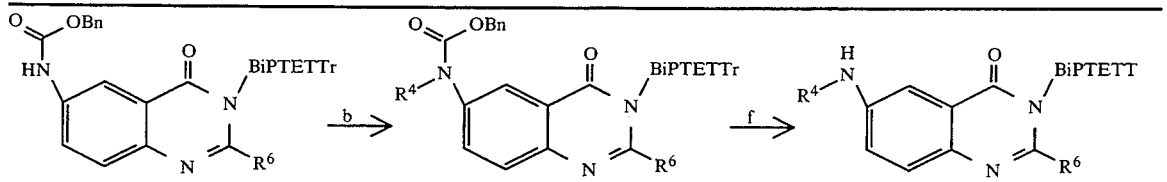

| ROUTE | PROCEDURE |
|---|---|
| A1 | d using $R^7$OCOCl |
| B1 | d using $R^8$ COCl |
| B2a | a,b. |
| B2b | a,c. |
| B2c | a,i. |
| B2d | a,j. |
| B2e | a,k |
| B2f | a,l. |
| B2g | a,m |
| B2h | h,a. |
| B2i | n,c |
| B2j | o,c. |
| B2k | p,c |

TABLE OF REAGENTS:
a. $R^8$COCl, $Et_3N$ or $iPr_2NEt$, DMAP in $CH_2Cl_2$ or $R^8$COCl, $K_2CO_3$ in dioxane, or NaH, $R^8$COCl in DMF
b. $LiNTMS_2$, $R^4I$ or $R^4Br$ or $R^4Cl$, DMF.
c. $Bu^4NHSO_4$, toluene, $K_2CO_3$, $R^4I$ or $R^4Br$ or $R^4Cl$.
d. NaH, $R^7$OCOCl or $R^8$COCl then $LiNTMS_2$, $R^4I$/DMF
f. $H_2$, 10% Pd/C.
h. $R^4$CHO, toluene, heat then $NaBH_4$, in dioxane/$Et_2O$
i. NaH, DMF, $R^4I$, or $R^4Br$ or $R^4Cl$.
j. t-BuOK, DMF, $R^4I$, $R^4Br$ or $R^4Cl$
k. $K_2CO_3$, DMF, $nBu_4NBr$, $R^4I$, $R^4Br$ or $R^4Cl$
l. $nBu_4NBr$, $CH_2Cl_2$, NaOH 50%, $R^4I$, $R^4Br$ or $R^4Cl$
m. $NaN(TMS)_2$, DMF, $R^4I$ or $R^4Br$ or $R^4Cl$.
n. NaOH, $R^8$COCl, $CH_2Cl^2$,
o. NaH, $R^8$COCl, DMF.
p. EDC, HOBt, $R^8$COOH Experimental Directions for General Synthetic Routes to 6-Substituted quinazolinones of Formula 1

Route A1

Step d:

To a suspension of 1.1 eq. of 80% NaH in a volume of dry DMF that would make a 0.1M solution was added at 0° C. under $N_2$ a solution of 1.0 eq. the requisite 6-amino-quinazolin-4(3H)-one dissolved in a minimal amount of DMF. After 30 min the chloroformate (ClCOOR⁷) of choice was added neat. The reaction mixture was stirred for 30 minutes. To this mixture was added 1.2 eq of a 1M solution of lithium hexamethyl-disilazide in THF. After 30 min. at 0° C. the alkylating agent ($R^4X$), described above, was added neat and the reaction mixture was stirred overnight allowing the temperature to increase to room temperature. The reaction mixture was diluted with EtOAc (10 times the volume of DMF used) and washed with water (3×25% volume EtOAc used) and brine. The solution was dried over $MgSO_4$, filtered and concentrated in vacuo. The residue was purified by flash chromatography over silica gel eluting with a mixture of 20–50% EtOAc/hexanes to give the carbamate in 50–70% yield.

Route B1

Step d:

The method of Route A1 was followed acylating with an acid chloride ($R^8$COCl) in place of the chloroformate $R^7CO_2Cl$ to give an amide.

Route B2a

Step a:

To a suspension of 0.48 mmol of 80% NaH in 2 ml of dry DMF was added at 0° C. under $N_2$ a solution of 0.44 mmol of 6-amino-2-alkyl-3-[(2'-(N-triphenylmethyl-tetrazol-5-yl)-biphen-4-yl)-methyl]-quinazolin-4(3H)-one in 1 ml of dry DMF. After 1 hour the acid chloride was added neat and the reaction mixture was stirred over night at room temperature. The reaction mixture was diluted with 50 ml of EtOAc and washed with water (3×10 ml) and brine (1×10 ml) and dried over $MgSO_4$. The suspension was filtered and concentrated in vacuo and the residue was purified by flash chromatography over silica gel eluting with an appropriate mixture of EtOAc/hexanes. 50% yield.

Alternatively the amine can be acylated by following: To a solution of 1.4 mmol of 6-amino-2-alkyl-3-[(2'-(N-triphenylmethyl-tetrazol-5-yl)-biphen-4-yl)-methyl]-quinazolin-4(3H)-one in 5 ml of dry dichloroethane under $N_2$ was added 8.6 mmol of triethyl amine, 20 mg of dimethylamino-pyridine and 2.1 mmol of the acyl halide. The reaction mixture was warmed to 60° C. over 48 hours, cooled and diluted with 100 ml of $CH_2Cl_2$ and washed with water (2×20 ml), brine (1×20 ml) and dried over $MgSO_4$. The reaction mixture was filtered and concentrated in vacuo and the residue was purified by flash chromatography over silica gel.

Alternatively the amine can be acylated by following: To a s solution of 6-amino-2-alkyl-3-[(2'-(N-triphenyl-methyl-tetrazol-5-yl)-biphen-4-yl)methyl]-quinazolin-4(3H)-one.(0.49 mmol) in dioxane powdered $K_2CO_3$ (7.8 mmol) was added followed by acyl chloride (0.58 mmol). After 1 hr the reaction mixture was diluted with water and the product was extracted with AcOEt. Concentration in vacuo was followed by purification of the product on silica gel by radial chromatography.

Step b:

To a solution of 0.4 mmol of the amide from Step B2a in 3 ml of dry DMF at 0° C. was added 0.44 mmol of a solution of lithium hexamethyl disilazide in hexanes.

After 10 minutes the reaction mixture was treated with the alkylating reagent of choice and the reaction mixture was allowed to warm to room temperature overnight. The solution was diluted with 25 ml of EtOAc and washed with water (3×5 ml) followed by brine and the organic phase was dried over MgSO4, filtered and concentrated in vacuo. The residue was purified by either flash chromatography or by radial chromatography to give the compound of choice.

Route B2b

Step a followed by Step c:

To a solution of 0.4 mmol of the amide from route B2a ('step a' above) in 3 ml of dry toluene was added 3.75 mmol of ground NaOH, 0.5 mmol of ground $K_2CO_3$ and 0.29 mmol of tetrabutyl ammonium hydrogen sulfate. To this mixture was added 0.8 mmol of the alkylating agent of choice and the reaction mixture was heated to 60° C. overnight. The mixture was diluted with 30 ml of EtOAc and washed with water (3×10 ml), brine (1×10 ml) and dried over MgSO4. The mixture was filtered, concentrated in vacuo and the residue was purified by flash chromatography over silica gel eluting with mixtures of EtOAc/hexanes to give the alkylated amide of choice.

Route B2c

Step a followed by Step i:

To a flask containing NaH (0.12 mmol, washed with hexane) a solution of the secondary amide from route B2a step a above (0.06 mmol) in DMF (1 ml) was cannulated and stirred at room temp. for 0.5 hr. The alkylating agent (0.09 mmol) was added in one portion and after 1 hr the reaction was quenched with addition of water and extracted with ethyl acetate. The oily residue obtained after concentrating the organic layer in vacuo was purified by radial chromatography on silica gel eluting with hexane/ethyl acetate to give the tertiary amide of choice.

Route B2d

Step a followed by Step j:

To a solution of the secondary amide from route B2a step a above (0.12 mmol) in dry DMF (2.0 ml) cooled to 0° C. t-BuOK (0.35 mmol) was added in one portion and after a few minutes alkylating agent was added. After overnight reaction at 0° C. the reaction mixture was diluted with water and extracted with $CH_2Cl_2$ and the tertiary amide of choise was purified by radial chromatography on silica gel eluting with hexane/ethyl acetate.

Route B2f

Step a followed by Step l:

To a solution of the secondary amide from route B2a step a above (0.082 mmol) in $CH_2Cl_2$ (2.0 ml) were added alkylating agent (0.84 mmol), (n-Bu)4NBr (0.1 equiv.) and 50% aq. NaOH solution. After vigorous stirring for 72 hrs the reaction mixture was diluted with water and extracted with CH2Cl2. The product was purified by radial chromatography on silica gel eluting with 1/1 hexane/ethyl acetate to give the tertiary amide of choice.

Route B2g

Step a followed by Step m:

To a solution of the secondary amide from route B2a step a above (0.28 mmol) in DMF (2.0 ml), cooled to 0° C., was added sodium hexamethyl-disilazide (1M in THF, 0.31 mmol) and after a few minutes the alkylating agent was added (in a small amount of DMF if solid). After stirring for 15 minutes at 0° C. the reaction mixture was diluted with water and extracted with ethyl acetate. The product was purified by radial chromatography on silica gel eluting with hexane/ethyl acetate.

Route B2h

Step h followed by step a Step h:

The solution of 6-amino-2-alkyl-3-[(2'-(N-triphenylmethyl-tetrazol-5-yl)-biphen-4-yl)-methyl]-quinazolin-4(3H)-one (0.25 mmol) and appropriate benzaldehyde (2.5 mmol) in dioxane was refluxed under $N_2$ until no starting amine is present by TLC. The reaction mixture was diluted with ethanol (5 ml) and sodium borohydride (3.15 mmol) was added portionwise with occasional warming. After 2 hrs the reaction mixture was diluted with water and extracted with $CH_2Cl_2$. The benzylamine of choice, was purified radial chromatography eluting with hexane/ethyl acetate.

Route B2i

Step n:

6-amino-2-alkyl-3-[(2'-(N-triphenylmethyl-tetrazol-5-yl)-biphen-4-yl)-methyl]-quinazolin-4(3H)-one was acylated with $R^8COCl$ under Schotten-Bauman conditions.

Followed by Step c.

Route B2j

Step o:

6-amino-2-alkyl-3-[(2'-(N-triphenylmethyl-tetrazol-5-yl)-biphen-4-yl)-methyl]-quinazolin-4(3H)-one was acylated as in the first part of Route B1.

Followed by step c.

Route B2k 6-amino-2-alkyl-3-[(2'-(N-triphenylmethyl-tetrazol-5-yl)-biphen-4-yl)-methyl]-quinazolin-4(3H)-one was acylated by $R^8COOH$ in the presence of 1.1 equivalents of 1-(3-dimethylaminopropyl)-3-ethylcarbodiimide hydrochloride, 1.2 equivalents of N,N-diisopropyl ethyl amine and 1.1 equivalents of N-hydroxy benzotriazole.

Followed by Step c.

TABLE 1

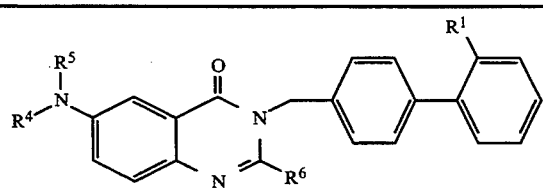

| Ex # | $R^6$ | $R^1$ | $R^5$ | $R^4$ | ROUTE |
|---|---|---|---|---|---|
| 1 | Et | TET | $CO_2iBn$ | Bn | A1 |

TABLE 1-continued

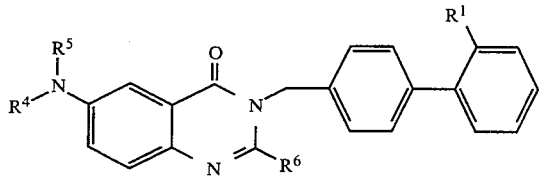

| Ex # | R6 | R1 | R5 | R4 | ROUTE |
|---|---|---|---|---|---|
| 2 | iBu | TET | CO2iBn | Bn | A1 |
| 3 | Me | TET | CO2iBu | Bn | A1 |
| 4 | Er | TET | CO2tBu | Bn | B2h |
| 5 | Et | TET | CO2Bn | Bn | B2h |
| 6 | Pr | TET | COPh-2-OPh | Bn | B2b |
| 7 | Pr | TET | COPh-4-OMe | Bn-4-OMe | B2b |
| 8 | Pr | TET | COPh-3,4,5-(OMe)3 | Bn | B2c |
| 9 | Pr | TET | COPh-2-OMe | Bn | B2c. |
| 10 | Pr | TET | COPh | Bn-4-Cl | B2a |
| 11 | Pr | TET | COPh-4-N3 | Bn | B2k. |
| 12 | Pr | TET | COPh | Bn-2-OMe | B2b. |
| 13 | Pr | TET | COPh | Bn-3,4-Cl2 | B2a |
| 14 | Pr | TET | COPh | Bn-2-OEt | B2a. |
| 15 | Pr | TET | COPh | Bn | B2a. |
| 16 | Pr | TET | COPh-3,4-Cl2 | Pn | B2j |
| 17 | Pr | TET | COPh | Bn-4-Me | B2g |
| 18 | Pr | TET | CO-2-furoyl | Bn | B2i |
| 19 | Pr | TET | CO-Pyrazine | Bn | B2k. |
| 20 | Et | TET | CO-2-thiophene | | |
| 21 | Pr | TET | COPh | Bn | B2a |
| 22 | Pr | TET | COPh-4-F | Bu | B2b |
| 23 | Pr | TET | COPh-4-Me | Pn | B2b. |
| 24 | Et | TET | COPh | Bn | B2h. |
| 25 | Et | TET | COPh-4-F | Pn | B2f |
| 26 | Et | TET | COPh-4-F | Bu | B2d |
| 27 | Et | TET | COPh | Bn-4-F | B2.h |
| 28 | c-Pr | TET | COPh | Bn | B2c |
| 29 | Me | TET | COPh | Bn | B2c |
| 30 | iPr | TET | COPh | Bn | B2c. |
| 31 | Et | TET | CO-4-Pyr | Bn | B2h. |
| 32 | Et | TET | COPh-2-Cl | Bn | B2c |
| 33 | Et | TET | COPh-2-Cl | Bn-2-Cl | B2c |
| 34 | Et | TET | COPh | Bn-2-Cl | B2c |
| 35 | Et | TET | COPh | CH2CH=CMe2 | B2c. |
| 36 | Et | TET | COPh | iPn | B2c |
| 37 | iPr | TET | COPh | Bn-2-Cl | B2c |
| 38 | iPr | TET | COcPr | Bn | B2c. |
| 39 | iPr | TET | COcPr | Bn-2-Cl | B2c |
| 40 | H | TET | COPh | Bn | B2c |
| 41 | Et | TET | COPh | Bn-4-Cl | B2c |
| 42 | Et | TET | COPh | Bn-2-F | B2c |
| 43 | Et | TET | COPh | Bn-3-Et | B2c |
| 44 | 1-methyl-propyl | TET | COPh | Bn | B2c |
| 45 | 1-methyl-propyl | TET | COPh | Bn-2-Cl | B2c. |
| 46 | Me | TET | CO-4-Pyr | Bn | B2c. |
| 47 | Me | TET | CO-4-pyr | Bn-2-Cl | B2g |
| 48 | Et | TET | COPh | Bn-4-I | B2g |
| 49 | iPr | TET | COPh | Bn-4-I | B2g |
| 50 | Et | TET | COPh-4-I | Bn | B2g |
| 51 | Et | TET | COPh | Bn-2-I | B2g. |
| 52 | Et | TET | CO-2-thiophene | Bn | B2c |
| 53 | CH2OMe | TET | COPh-4-Cl | Pn | B2.b |
| 54 | Pr | TET | CO-2-thiophene | Bn | B2c |
| 55 | Pr | TET | CO-3-pyr | Bn | B3 |
| 56 | Pr | TET | CO-2-pyr | Bn | B2a |
| 57 | Pr | TET | COPh | CH2-4-Pyr | B2a. |
| 58 | Pr | TET | CO-4-Pyr | Bn | B2a. |
| 59 | Me | TET | COPh | CH2-3-Pyr | B1 |
| 60 | Me | TET | COPh | CH2-2-Pyr | B2a |

Pharmaceutical Formulations

A: Dry Filled Capsules Containing 50 mg of Active Ingredient Per Capsule

| Ingredient | Amount per capsule (mg) |
| --- | --- |
| 2-Ethyl-6-(N-benzyl-N-2-thiophene-carbonyl)amino)-3[(2'-(tetrazol-5-yl)biphen-4-yl)methyl]-quinazolin-4(3H)-one (Example 52) | 50 |
| Lactose | 149 |
| Magnesium stearate | 1 |
| Capsule (size No. 1) | 200 |

The 2-ethyl-6-(N-benzyl-N-2-thiophenecarbonyl-)amino-3[(2'-(tetrazol-5-yl)biphen-4-yl)methyl]quinazolin-4(3H)-one (Example 52) can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain 2-ethyl-6-(N-benzyl-N-2-thiophenecarbonyl)amino-3[(2'-(tetrazol-5-yl)biphen-4-yl)methyl]-quinazolin-4(3H)-one (25 mg) (Example 52), pregelatinized starch USP (82 mg), microcrystalline cellulose (82 mg) and magnesium stearate (1 mg).

C: Combination Tablet

A typical combination tablet would contain, for example, a diuretic such as hydrochlorothiazide (25 mg) and 2-ethyl-6-(N-benzyl-N-2-thiophenecarbonyl-)amino-3-[(2'-(tetrazol-5-yl)biphen-4-yl)-methyl]-quinazolin-4(3H)-one (50 mg) (Example 52) pregelatinized starch USP (82 mg), microcrystalline cellulose (82 mg) and magnesium stearate (1 mg).

D: Suppository

Typical suppository formulations for rectal administration can contain 2-ethyl-6-(N-benzyl-N-thiophenecarbonyl)amino-3[(2'-(tetrazol-5-yl)-biphen-4-yl)methyl]quinazolin-4(3H)-one (0.08-1.0 mg), (Example 52) disodium calcium edetate (0.25-0.5 mg), and polyethylene glycol (775-1600 mg). Other suppository formulations can be made by substituting, for example, butylated hydroxytoluene (0.04-0.08 mg) for the disodium calcium edetate and a hydrogenated vegetable oil (675-1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotensin converting enzyme and/or a calcium channel blocker in pharmaceutically effective amounts as described, for example, in C above.

E: Injection

A typical injectable formulation would contain 2-ethyl-6-(N-benzyl-N-2-thiophenecarbonyl)amino-3-[(2'-(tetrazol-5-yl)biphen-4-yl)-methyl]quinazolin-4(3H)-one (Example 52) sodium phosphate dibasic anhydrous (11.4 mg) benzyl alcohol (0.01 ml) and water for injection (1.0 ml). Such an injectable formulation can also include a pharmaceutically effective amount of another active ingredient such as another antihypertensive and/or a diuretic and/or an angiotensin converting enzyme inhibitor and/or a calcium channel blocker.

What is claimed is:

1. A method of inhibiting vascular restenosis in a patient in need of a vascular surgery which comprises the administration of an $AT_2$ antagonist with intrinsic activity of $IC_{50} < 10$ nM prior to or at the time of the surgery and adminstration of the $AT_2$ antagonist for at least 6 months following the angioplasty, wherein the $AT_2$ antagonist is selected from the group consisting of the following compounds represented by Formula (I):

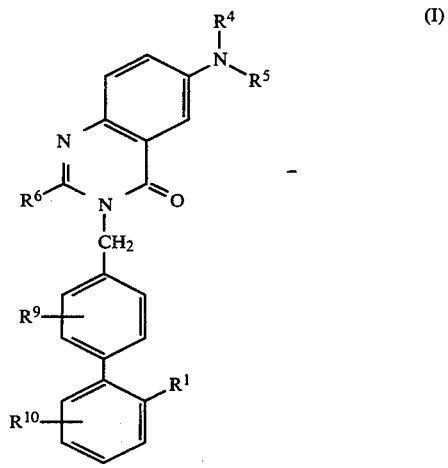

or a pharmaceutically acceptable salt thereof; wherein:

$R^1$ is
  (a) $CO_2R^2$, or
  (b) tetrazol-5-yl;

$R^2$ is
  (a) hydrogen, or
  (b) $C_1-C_6$ alkyl;

$R^4$ is
  (a) $C_1-C_6$ alkyl,
  (b) substituted $C_1-C_6$ alkyl in which the substituent is halo, $C_3-C_7$ cycloalkyl, $C_1-C_4$ alkoxy, hydroxy, di-($C_1-C_4$ alkyl)amino, morpholinyl, $C_1-C_4$ alkylpiperazinyl, $CF_3$, $C_1-C_4$ alkylthio, $C_1-C_4$ alkylsuffinyl, $C_1-C_4$ alkylsulfonyl, CHO, or $O(C_2-C_3\text{alkyl-O})_n-C_1-C_3$ alkyl, where n is 1-5,
  (c) $C_2-C_6$ alkenyl,
  (d) phenyl $C_1-C_6$ alkyl, or
  (e) heteroaryl $C_1-C_6$ alkyl;

$R^5$ is
  (a) $CO_2R^7$, or
  (b) $COR^8$;

$R^6$ is
  (a) H,
  (b) methyl,
  (c) ethyl,
  (d) $C_4-C_6$ alkyl, excluding linear alkyl,
  (e) $C_1-C_6$ cycloalkyl, or
  (f) $C_1-C_6$ alkyl, substituted with $C_1-C_4$ alkoxy;

$R^7$ is
  (a) $C_1-C_6$ alkyl,
  (b) substituted $C_1-C_6$ alkyl, in which the substituent is $C_1-C_4$ alkoxy, hydroxy, halo, di-($C_1-C_4$ alkyl)amino, morpholinyl, $C_1-C_4$ alkylpiperazinyl, $C_1-C_4$ alkylsulfinyl, $C_1-C_4$ alkylsulfonyl, $C_1-C_4$ alkylthio, or $O(C_2-C_3\text{alkylO})_n-C_1-C_3$ alkyl, $C_3-C_7$ cycloalkyl wherein n=1-5,
  (c) phenyl $C_1-C_6$ alkyl, or
  (d) heteroaryl $C_1-C_6$ alkyl;

$R^8$ is (a) phenyl,
(b) phenyl $C_1$–$C_6$ alkyl,
(c) heteroaryl,
(d) heteroaryl $C_1$–$C_6$ alkyl,
(e) $C_1$–$C_6$ alkyl,
(f) substituted $C_1$–$C_6$ alkyl in which the substituent is halo, $C_3$–$C_7$ cycloalkyl, $C_1$–$C_4$ alkoxy, hydroxy, di-($C_1$–$C_4$ alkyl)amino, morpholinyl, $C_1$–$C_4$ alkylpiperazinyl, $CF_3$, $C_1$–$C_4$ alkylthio, $C_1$–$C_4$ alkylsulfinyl, $C_1$–$C_4$ alkylsulfonyl, imidazolyl, —N(CO$C_1$–$C_6$ alkyl) piperazinyl, N-aryl piperazinyl, or
(g) $C_3$–$C_7$ cycloalkyl;

$R^9$ is
(a) hydrogen,
(b) F, Cl Br or I,
(c) $C_1$–$C_4$ alkyl, or
(d) $C_1$–$C_6$ alkoxy;

$R^{10}$ is
(a) hydrogen,
(b) $C_1$–$C_5$ alkyl, or
(c) phenyl.

2. The method of claim 1 wherein $R^5$ is $CO_2R^7$.
3. The method of claim 2 wherein:
$R^1$ is tetrazol-5-yl,
$R^4$ is
(a) $C_2$–$C_6$ alkyl,
(b) substituted $C_2$–$C_6$ alkyl in which the substituent is: $OC_1$–$C_4$ alkyl, cyclohexyl, or phenyl,
(c) benzyl,
(d) substituted benzyl in which the substituent on the phenyl group is: F, Cl Br, I, OH, $OC_1$–$C_4$alkyl, $NO_2$, $NH_2$, or $N(C_1$–$C_4$ alkyl$)_2$,
(e) $CH_2$-heteroaryl or
(f) $C_3$–$C_6$ alkenyl;

$R^6$ is
(a) methyl, ethyl,
(b) non-linear substituted $C_1$–$C_6$ alkyl in which the substituent is: -benzyl, -$C_1$–$C_3$ alkyl, or -$OC_1$–$C_4$alkyl, or
(c) cyclopropyl;

$R^7$ is
(a) $C_1$–$C_6$ alkyl,
(b) benzyl, or
(c) $C_2$–$C_4$ alkyl-O—$C_1$–$C_4$ alkyl.

4. The method of claim 3 wherein said compound is selected from the group consisting of the compounds depicted in the following Table:

| $R^6$ | $R^1$ | $R^7$ | $R^4$ |
|---|---|---|---|
| Et | TET | iBu | Bn |
| iBu | TET | iBu | Bn |
| Me | TET | iBu | Bn |
| Et | TET | t-Bu | Bn |
| Et | TET | Bn | Bn. |

5. The method of claim 1 wherein $R^5$ is $COR^8$.
6. The method of claim 5 wherein:
$R^1$ is tetrazol-5-yl,
$R^4$ is
(a) $C_3$–$C_6$ alkyl,
(b) substituted $C_3$–$C_6$ alkyl in which the substituent is: $OC_1$–$C_4$ alkyl, cyclohexyl, phenyl,
(c) benzyl,
(d) substituted benzyl in which the substituent on the phenyl group is: F, Cl Br, I, OH, $NO_2$, $NH_2$, $N(C_1$–$C_4$ alkyl$)_2$, O-benzyl, O—$C_1$–$C_4$ alkyl, or O-phenyl;
(e) $CH_2$-heteroaryl, or
(f) $C_3$–$C_6$ alkenyl;

$R^6$ is
(a) methyl,
(b) ethyl,
(c) isopropyl,
(d) isobutyl,
(e) 1-ethylpropyl,
(f) $CH_2OMe$,
(g) cyclopropyl, or
(h) propyl;

$R^{10}$ is
(a) phenyl,
(b) substituted phenyl in which the substituent is F, Cl Br, I, methoxy, methyl, $CF_3$, SMe, OH, O-Benzyl or O-phenyl; or
(c) heteroaryl.

7. The method of claim 6 wherein said compound is selected from the group consisting of compounds depicted in the following table:

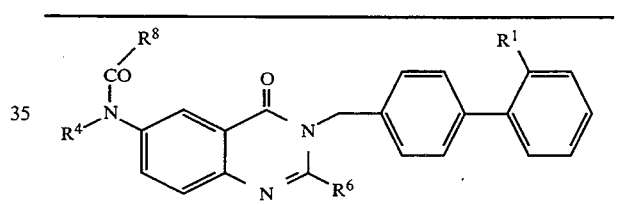

| $R^6$ | $R^1$ | $R^8$ | $R^4$ |
|---|---|---|---|
| Pr | TET | Ph-2-OPh | Bn |
| Pr | TET | Ph-4-OMe | Bn-4-OMe |
| Pr | TET | Ph-3,4,5-(OMe)$_3$ | Bn |
| Pr | TET | Ph-2-OMe | Bn |
| Et | TET | 2-thiophenyl | Bn |
| Pr | TET | Ph | Bn-4-Cl |
| Pr | TET | Ph-4-N3 | Bn |
| Pr | TET | Ph | Bn-2-OMe |
| Pr | TET | Ph | Bn-3,4-Cl |
| Pr | TET | Ph | Bn-2-OEt |
| Pr | TET | Ph | Bn |
| Pr | TET | Ph-3,4-Cl$_2$ | Pn |
| Pr | TET | Ph | Bn-4-Me |
| Pr | TET | 2-furoyl | Bn |
| Pr | TET | Pyrazinyl | Bn |
| Et | TET | 2-thiophenyl | (4-hydroxy-3-iodo)-pyridyl-2-methyl iodo |
| Pr | TET | Ph | Bn |
| Pr | TET | Ph-4-F | Bu |
| Pr | TET | Ph-4-Me | Pn |
| Et | TET | Ph | Bn |
| Et | TET | Ph-4-F | Pn |
| Et | TET | Ph-4-F | Bu |
| Et | TET | Ph | Bn-4-F |
| c-Pr | TET | Ph | Bn |
| Me | TET | Ph | Bn |
| iPr | TET | Ph | Bn |
| Et | TET | 4-Pyr | Bn |
| Et | TET | Ph-2-Cl | Bn |
| Et | TET | Ph-2-Cl | Bn-2-Cl |
| Et | TET | Ph | Bn-2-Cl |
| Et | TET | Ph | $CH_2CH$=$CMe_2$ |
| Et | TET | Ph | iPn |
| iPr | TET | Ph | Bn-2-Cl |

-continued

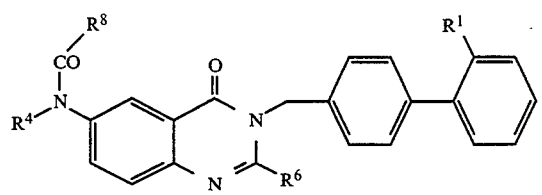

| R6 | R1 | R8 | R4 |
|---|---|---|---|
| iPr | TET | cPr | Bn |
| iPr | TET | cPr | Bn-2-Cl |
| H | TET | Ph | Bn |
| Et | TET | Ph | Bn-4-Cl |
| Et | TET | Ph | Bn-4-F |
| Et | TET | Ph | Bn-3-Et |
| 1-methyl-propyl | TET | Ph | Bn |
| 1-methyl-propyl | TET | Ph | Bn-2-Cl |
| Me | TET | 4-Pyr | Bn |
| Me | TET | 4-Pyr | Bn-2-Cl |
| Et | TET | Ph | Bn-4-I |
| iPr | TET | Ph | Bn-4-I |
| Et | TET | Ph-4-I | Bn |

-continued

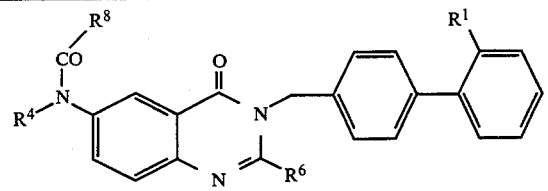

| R6 | R1 | R8 | R4 |
|---|---|---|---|
| Et | TET | Ph | Bz-2-I |
| Et | TET | 2-thienyl | Bn |
| CH2OMe | TET | Ph-4-Cl | Pn |
| Pr | TET | 2-thienyl | Bn |
| Pr | TET | 3-Pyr | Bn |
| Pr | TET | 2-Pyr | Bn |
| Pr | TET | Ph | CH2-4-Pyr |
| Pr | TET | 4-Pyr | Bn |
| Me | TET | Ph | CH2-3-Pyr |
| Me | TET | Ph | CH2-2-Pyr. |

8. The method of claim 1, wherein the amount of $AT_2$ antagonist delivered at or prior to the time of the vascular surgery is 50 to 200 mg/kg and following angioplasty is 50 to 200 mg/kg/day.

9. The method of claim 1 for inhibiting vascular restenosis in a patient in need of vascular surgery which further comprises the administration of heparin in combination with the $AT_2$ antagonist.

10. The method of claim 9, wherein the amount of heparin delivered at or prior to the time of vascular surgery is about 15,000 to 45,000 units/kg/day (140–170 USP units/mg).

* * * * *